(12) United States Patent
Lahti et al.

(10) Patent No.: US 11,766,238 B2
(45) Date of Patent: Sep. 26, 2023

(54) MEASUREMENT NAVIGATION IN A MULTI-MODALITY MEDICAL IMAGING SYSTEM

(71) Applicant: PHILIPS IMAGE GUIDED THERAPY CORPORATION, San Diego, CA (US)

(72) Inventors: Douglas G. Lahti, San Diego, CA (US); Asher Cohen, Sacramento, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 320 days.

(21) Appl. No.: 17/068,716

(22) Filed: Oct. 12, 2020

(65) Prior Publication Data

US 2021/0038188 A1 Feb. 11, 2021

Related U.S. Application Data

(63) Continuation of application No. 14/135,263, filed on Dec. 19, 2013, now Pat. No. 10,799,209.

(Continued)

(51) Int. Cl.
*A61B 8/12* (2006.01)
*A61B 5/00* (2006.01)
(Continued)

(52) U.S. Cl.
CPC ............ *A61B 8/12* (2013.01); *A61B 5/0035* (2013.01); *A61B 5/0066* (2013.01); *A61B 5/742* (2013.01);
(Continued)

(58) Field of Classification Search
CPC ....... A61B 8/12; A61B 5/0035; A61B 5/0066; A61B 5/742; A61B 5/7485; A61B 8/0891;
(Continued)

(56) References Cited

U.S. PATENT DOCUMENTS 5,081,695 A  1/1992  Gould
6,200,268 B1  3/2001  Vince
(Continued)

FOREIGN PATENT DOCUMENTS

JP  2002049908 A  2/2002
JP  2007029341 A  2/2007
KR  2009075555 A  7/2009

*Primary Examiner* — Eliza A Lam

(57) ABSTRACT

Systems and methods for multi-modality data processing are provided. Some embodiments are particularly directed to navigating sets of multi-modality medical data in a multi-modality processing system. In one embodiment, a method for navigating medical data in a medical processing system includes receiving a reference set of medical data by the medical processing system, where the medical data corresponds to a modality selected from the group consisting of: FFR, iFR, pressure, flow, IVUS, and OCT. The medical processing system also receives a navigation command. An enhancement and a subset of the reference set of medical data to enhance are identified based on the navigation command. The medical processing system performs the selected enhancement on the subset of data and the enhanced subset is displayed. The enhancement may include performing a single-axis zoom on the subset.

10 Claims, 13 Drawing Sheets

Related U.S. Application Data

(60) Provisional application No. 61/745,986, filed on Dec. 26, 2012.

(51) Int. Cl.
| | | |
|---|---|---|
| *A61B 8/00* | (2006.01) | |
| *G06F 3/04883* | (2022.01) | |
| *A61B 8/08* | (2006.01) | |
| *G16H 30/20* | (2018.01) | |
| *G16H 30/40* | (2018.01) | |
| *A61B 5/0215* | (2006.01) | |
| *A61B 5/026* | (2006.01) | |

(52) U.S. Cl.
CPC .......... *A61B 5/7485* (2013.01); *A61B 8/0891* (2013.01); *A61B 8/463* (2013.01); *A61B 8/465* (2013.01); *G06F 3/04883* (2013.01); *G16H 30/20* (2018.01); *G16H 30/40* (2018.01); *A61B 5/026* (2013.01); *A61B 5/0215* (2013.01); *A61B 8/467* (2013.01); *A61B 8/565* (2013.01)

(58) Field of Classification Search
CPC ....... A61B 8/463; A61B 8/465; A61B 5/0215; A61B 5/026; A61B 8/467; A61B 8/565; G06F 3/04883; G16H 30/20; G16H 30/40
See application file for complete search history.

(56) References Cited

U.S. PATENT DOCUMENTS

| | | | |
|---|---|---|---|
| 6,381,350 | B1 | 4/2002 | Klingensmith |
| 7,074,188 | B2 | 7/2006 | Nair |
| 7,175,597 | B2 | 2/2007 | Vince |
| 7,215,802 | B2 | 5/2007 | Klingensmith |
| 7,359,554 | B2 | 4/2008 | Klingensmith |
| 7,463,759 | B2 | 12/2008 | Klingensmith |
| 7,930,012 | B2 | 4/2011 | Huennekens |
| 8,131,051 | B2 * | 3/2012 | Heath ............... G06T 5/008 |
| | | | 382/274 |
| 8,625,869 | B2 | 1/2014 | Harder |
| 2002/0193677 | A1 | 12/2002 | Thornton |
| 2004/0015079 | A1 * | 1/2004 | Berger ............ A61B 8/0841 |
| | | | 600/443 |
| 2005/0251020 | A1 | 11/2005 | Kondo |
| 2007/0038061 | A1 | 2/2007 | Huennekens |
| 2007/0160275 | A1 | 7/2007 | Sathyanarayana |
| 2007/0260141 | A1 | 11/2007 | Margolis |
| 2008/0272304 | A1 | 11/2008 | Vija |
| 2009/0087049 | A1 | 4/2009 | Takahashi |
| 2010/0009239 | A1 | 1/2010 | Shibata |
| 2010/0067753 | A1 | 3/2010 | Visser |
| 2011/0306867 | A1 * | 12/2011 | Gopinathan ......... A61B 5/068 |
| | | | 600/407 |
| 2012/0071782 | A1 * | 3/2012 | Patil ............... G01R 19/2513 |
| | | | 702/65 |
| 2013/0120296 | A1 * | 5/2013 | Merritt ............... G06F 3/041 |
| | | | 345/173 |

* cited by examiner

MEASUREMENT NAVIGATION IN A MULTI-MODALITY MEDICAL IMAGING SYSTEM

CROSS-REFERENCE TO RELATED APPLICATIONS

The present application is a continuation of U.S. patent application Ser. No. 14/135,263, filed Dec. 19, 2013, now U.S. Pat. No. 10,799,209, which claims priority to and the benefit of U.S. Provisional Patent Application No. 61/745,986, filed Dec. 26, 2012, each of which is hereby incorporated by reference in its entirety.

TECHNICAL FIELD

The present disclosure relates generally to the field of medical devices and, more particularly, to data collection, manipulation, enhancement, display, and annotation in a multi-modality medical system.

BACKGROUND

Innovations in diagnosing and verifying the level of success of treatment of disease have migrated from external imaging processes to internal diagnostic processes. In particular, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include angiography, intravascular ultrasound (IVUS), forward looking IVUS (FL-IVUS), fractional flow reserve (FFR) determination, a coronary flow reserve (CFR) determination, optical coherence tomography (OCT), transesophageal echocardiography, and image-guided therapy. Each of these techniques may be better suited for different diagnostic situations. To increase the chance of successful treatment, health care facilities may have a multitude of imaging, treatment, diagnostic, and sensing modalities on hand in a catheter lab during a procedure. Recently, processing systems have been designed that collect medical data from a plurality of different imaging, treatment, diagnostic, and sensing tools and process the multi-modality medical data. Such multi-component systems often include modules that depend on each other for information and system services.

While existing multi-modality medical processing systems have proved useful, there remains a need for improvements in data handling and processing. For example, improvements to data identification have the potential to enhance the ability to recognize, separate, index, and catalog relevant data. Improved methods and interfaces for presenting data collected across modalities in a unified, coherent fashion may allow operators to draw accurate diagnostic conclusions. Further interface improvements may allow operators to better refine, enhance, and measure data collected across modalities.

SUMMARY

Embodiments of the present disclosure provide an enhanced system and method for navigating sets of medical data in a multi-modality processing system.

In some embodiments, a method for interpreting user input in a medical processing system is provided. The method includes receiving a reference set of medical data by the medical processing system, where the medical data corresponds to a first modality selected from the group of modalities consisting of: FFR, iFR, pressure, flow, IVUS, and OCT. The medical processing system also receives a navigation command. An enhancement and a subset of the reference set of data are identified based on the navigation command. The medical processing system performs the selected enhancement on the subset, and the enhanced subset is displayed. In one such embodiment, the navigation command designates an additional set of medical data corresponding to a second modality different from the first modality. In another such embodiment, the performing of the enhancement includes performing a single-axis zoom on the subset.

In some embodiments, an apparatus is disclosed. The apparatus includes a non-transitory, computer-readable storage medium that stores a plurality of instructions for execution by at least one computer processor, wherein the instructions are for: receiving a reference set of medical data corresponding to a first modality selected from the group of modalities consisting of: FFR, iFR, pressure, flow, IVUS, and OCT; receiving a navigation command; performing an enhancement on a subset of the reference set as specified by the navigation command; and providing the enhanced subset for display. In one such embodiment, the instructions for the receiving of the navigation command include instructions for: receiving a user input sequence indicating a first touch-based input concurrent with a second touch-based input; and translating the user input sequence into the navigation command. In the above embodiment, the navigation command designates a first boundary of the subset corresponding to the first touch-based input and a second boundary of the subset corresponding to the second touch-based input.

In some embodiments, a medical processing system is disclosed. The medical processing system includes a medical data interface configured to receive a reference set of medical data and a navigator engine. The navigator engine is configured to receive a navigation command from a controller; identify an enhancement to perform based on the navigation command; identify a subset of the reference set of medical data to enhance based on the navigation command; perform the identified enhancement on the identified subset; and provide the enhanced subset for display. In one such embodiment, the navigator engine is further configured to provide an update for a display of the reference set of medical data based on the navigation command.

The systems and methods of the present disclosure perform on-demand enhancement and measurement of medical data in a multi-modality environment. In some embodiments, an operator may select areas or information to enhance, creating larger, clearer, and more accurate views. In some embodiments, an enhanced view is provided by applying a single-axis zoom to a subset of the medical data. A single-axis zoom allows data to be rescaled along a first axis without necessarily rescaling the data along a second. This is particularly useful for, but not limited to, medical data sets that include data values plotted over a range of time or distance, where the data values are periodic. In such data, the peak-to-peak extremes along one axis might not vary substantially as the scaling of the second axis is adjusted. The single-axis zoom is merely one enhancement by which the embodiments of the present disclosure provide an improved interface for navigating and manipulating data sets in a manner responsive to the nature of the underlying data.

Of course, it is understood that these advantages are merely exemplary, and no particular advantage is required for any particular embodiment.

Additional aspects, features, and advantages of the present disclosure will become apparent from the following detailed description.

DETAILED DESCRIPTION

Figure 1:
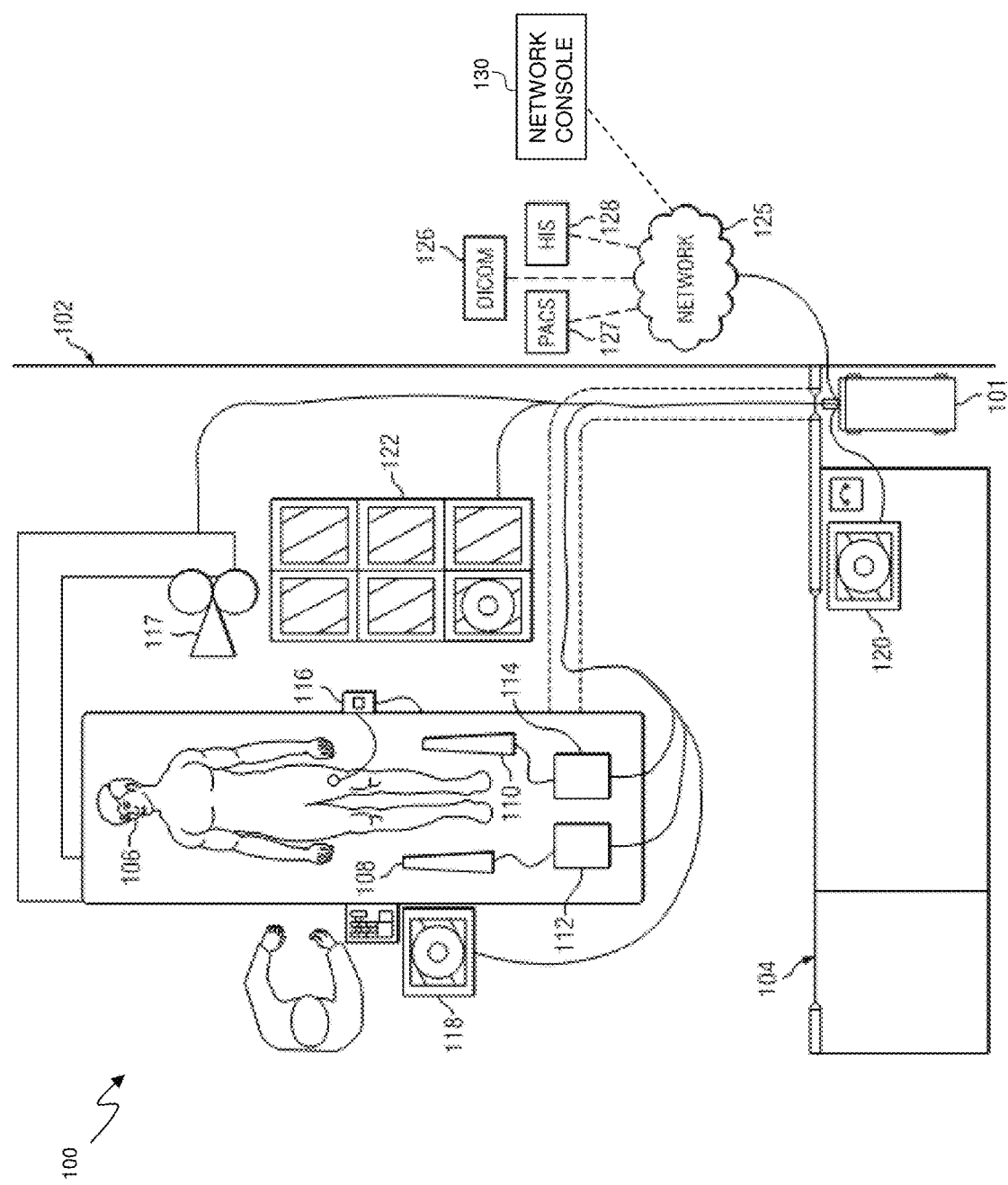
FIG. 1 is a schematic drawing depicting a medical system including a multi-modality processing system according to some embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic drawing depicting a medical system 100 including a multi-modality processing system 101 according to one embodiment of the present disclosure. In general, the medical system 100 provides for coherent integration and consolidation of multiple forms of acquisition and processing elements designed to be sensitive to a variety of methods used to acquire and interpret human biological physiology and morphological information and coordinate treatment of various conditions. More specifically, in system 100, the multi-modality processing system 101 is an integrated device for the acquisition, control, interpretation, and display of multi-modality medical sensing data. In one embodiment, the processing system 101 is a computer system with the hardware and software to acquire, process, and display multi-modality medical data, but, in other embodiments, the processing system 101 may be any other type of computing system operable to process medical data. In the embodiments in which processing system 101 is a computer workstation, the system includes at least a processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and a network communication device such as an Ethernet controller or wireless communication controller. In that regard, in some particular instances the processing system 101 is programmed to execute steps associated with the data acquisition and analysis described herein. Accordingly, it is understood that any steps related to data acquisition, data processing, instrument control, and/or other processing or control aspects of the present disclosure may be implemented by the processing system using corresponding instructions stored on or in a non-transitory computer readable medium accessible by the processing system. In some instances, the processing system 101 is portable (e.g., handheld, on a rolling cart, etc.). Further, it is understood that in some instances processing system 101 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

In the illustrated embodiment, the medical system 100 is deployed in a catheter lab 102 having a control room 104, with the processing system 101 being located in the control room. In other embodiments, the processing system 101 may be located elsewhere, such as in the catheter lab 102, in a centralized area in a medical facility, or at an off-site location (i.e., in the cloud). The catheter lab 102 includes a sterile field generally encompassing a procedure area but its associated control room 104 may or may not be sterile depending on the requirements of a procedure and/or health care facility. The catheter lab and control room may be used to perform on a patient any number of medical sensing procedures such as angiography, intravascular ultrasound (IVUS), virtual histology (VH), forward looking IVUS (FL-IVUS), intravascular photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intravascular palpography, transesophageal ultrasound, or any other medical sensing modalities known in the art. Further, the catheter lab and control room may be used to perform one or more treatment or therapy procedures on a patient such as radiofrequency ablation (RFA), cryotherapy, atherectomy or any other medical treatment procedure known in the art. For example, in catheter lab 102 a patient 106 may be undergoing a multi-modality procedure either as a single procedure or in combination with one or more sensing procedures. In any case, the catheter lab 102 includes a plurality of medical instruments including medical sensing devices that may collect medical sensing data in various different medical sensing modalities from the patient 106.

In the illustrated embodiment of FIG. 1, instruments 108 and 110 are medical sensing devices that may be utilized by a clinician to acquire medical sensing data about the patient 106. In a particular instance, the device 108 collects medical sensing data in one modality and the device 110 collects medical sensing data in a different modality. For instance, the instruments may each collect one of pressure, flow (velocity), images (including images obtained using ultrasound (e.g., IVUS), OCT, thermal, and/or other imaging techniques), temperature, and/or combinations thereof. The devices 108 and 110 may be any form of device, instrument, or probe sized and shaped to be positioned within a vessel, attached to an exterior of the patient, or scanned across a patient at a distance.

In the illustrated embodiment of FIG. 1, instrument 108 is an IVUS catheter 108 that may include one or more sensors such as a phased-array transducer to collect IVUS sensing data. In some embodiments, the IVUS catheter 108 may be capable of multi-modality sensing such as IVUS and IVPA sensing. Further, in the illustrated embodiment, the instrument 110 is an OCT catheter 110 that may include one or more optical sensors configured to collect OCT sensing data. In some instances, an IVUS patient interface module (PIM) 112 and an OCT PIM 114 respectively couple the IVUS catheter 108 and OCT catheter 110 to the medical system 100. In particular, the IVUS PIM 112 and the OCT PIM 114 are operable to respectively receive medical sensing data collected from the patient 106 by the IVUS catheter 108 and OCT catheter 110 and are operable to transmit the received data to the processing system 101 in the control room 104. In one embodiment, the PIMs 112 and 114 include analog to digital (A/D) converters and transmit digital data to the processing system 101, however, in other embodiments, the PIMs transmit analog data to the processing system. In one embodiment, the IVUS PIM 112 and OCT PIM 114 transmit the medical sensing data over a Peripheral Component Interconnect Express (PCIe) data bus connection, but, in other embodiments, they may transmit data over a USB connection, a Thunderbolt connection, a FireWire connection, or some other high-speed data bus connection. In other instances, the PIMs may be connected to the processing system 101 via wireless connections using IEEE 802.11 Wi-Fi standards, Ultra Wide-Band (UWB) standards, wireless FireWire, wireless USB, or another high-speed wireless networking standard.

Additionally, in the medical system 100, an electrocardiogram (ECG) device 116 is operable to transmit electrocardiogram signals or other hemodynamic data from patient 106 to the processing system 101. In some embodiments, the processing system 101 may be operable to synchronize data collected with the catheters 108 and 110 using ECG signals from the ECG 116. Further, an angiogram system 117 is operable to collect x-ray, computed tomography (CT), or magnetic resonance images (MRI) of the patient 106 and transmit them to the processing system 101. In one embodiment, the angiogram system 117 may be communicatively coupled to the processing system to the processing system 101 through an adapter device. Such an adaptor device may transform data from a proprietary third-party format into a format usable by the processing system 101. In some embodiments, the processing system 101 may be operable to co-register image data from angiogram system 117 (e.g., x-ray data, MRI data, CT data, etc.) with sensing data from the IVUS and OCT catheters 108 and 110. As one aspect of this, the co-registration may be performed to generate three-dimensional images with the sensing data.

A bedside controller 118 is also communicatively coupled to the processing system 101 and provides user control of the particular medical modality (or modalities) being used to diagnose the patient 106. In the current embodiment, the bedside controller 118 is a touch screen controller that provides user controls and diagnostic images on a single surface. In alternative embodiments, however, the bedside controller 118 may include both a non-interactive display and separate controls such as physical buttons and/or a joystick. In the integrated medical system 100, the bedside controller 118 is operable to present workflow control options and patient image data in graphical user interfaces (GUIs). As will be described in greater detail in association with FIG. 2, the bedside controller 118 includes a user interface (UI) framework service through which workflows associated with multiple modalities may execute. Thus, the bedside controller 118 is capable displaying workflows and diagnostic images for multiple modalities allowing a clinician to control the acquisition of multi-modality medical sensing data with a single interface device.

A main controller 120 in the control room 104 is also communicatively coupled to the processing system 101 and, as shown in FIG. 1, is adjacent to catheter lab 102. In the current embodiment, the main controller 120 is similar to the bedside controller 118 in that it includes a touch screen and is operable to display multitude of GUI-based workflows corresponding to different medical sensing modalities via a UI framework service executing thereon. In some embodiments, the main controller 120 may be used to simultaneously carry out a different aspect of a procedure's workflow than the bedside controller 118. In alternative embodiments, the main controller 120 may include a non-interactive display and standalone controls such as a mouse and keyboard.

The medical system 100 further includes a boom display 122 communicatively coupled to the processing system 101. The boom display 122 may include an array of monitors, each capable of displaying different information associated with a medical sensing procedure. For example, during an IVUS procedure, one monitor in the boom display 122 may display a tomographic view and one monitor may display a sagittal view.

Further, the multi-modality processing system 101 is communicatively coupled to a data network 125. In the illustrated embodiment, the data network 125 is a TCP/IP-based local area network (LAN); however, in other embodiments, it may utilize a different protocol such as Synchronous Optical Networking (SONET), or may be a wide area network (WAN). The processing system 101 may connect to various resources via the network 125. For example, the processing system 101 may communicate with a Digital Imaging and Communications in Medicine (DICOM) system 126, a Picture Archiving and Communication System (PACS) 127, and a Hospital Information System (HIS) 128 through the network 125. Additionally, in some embodiments, a network console 130 may communicate with the multi-modality processing system 101 via the network 125 to allow a doctor or other health professional to access the aspects of the medical system 100 remotely. For instance, a user of the network console 130 may access patient medical data such as diagnostic images collected by multi-modality processing system 101, or, in some embodiments, may monitor or control one or more on-going procedures in the catheter lab 102 in real-time. The network console 130 may be any sort of computing device with a network connection such as a PC, laptop, smartphone, tablet computer, or other such device located inside or outside of a health care facility.

Additionally, in the illustrated embodiment, medical sensing tools in system 100 discussed above are shown as communicatively coupled to the processing system 101 via a wired connection such as a standard copper link or a fiber optic link, but, in alternative embodiments, the tools may be connected to the processing system 101 via wireless connections using IEEE 802.11 Wi-Fi standards, Ultra Wide-Band (UWB) standards, wireless FireWire, wireless USB, or another high-speed wireless networking standard.

One of ordinary skill in the art would recognize that the medical system 100 described above is simply an example embodiment of a system that is operable to collect diagnostic data associated with a plurality of medical modalities. In alternative embodiments, different and/or additional tools may be communicatively coupled to the processing system 101 so as to contribute additional and/or different functionality to the medical system 100.

Figure 2:
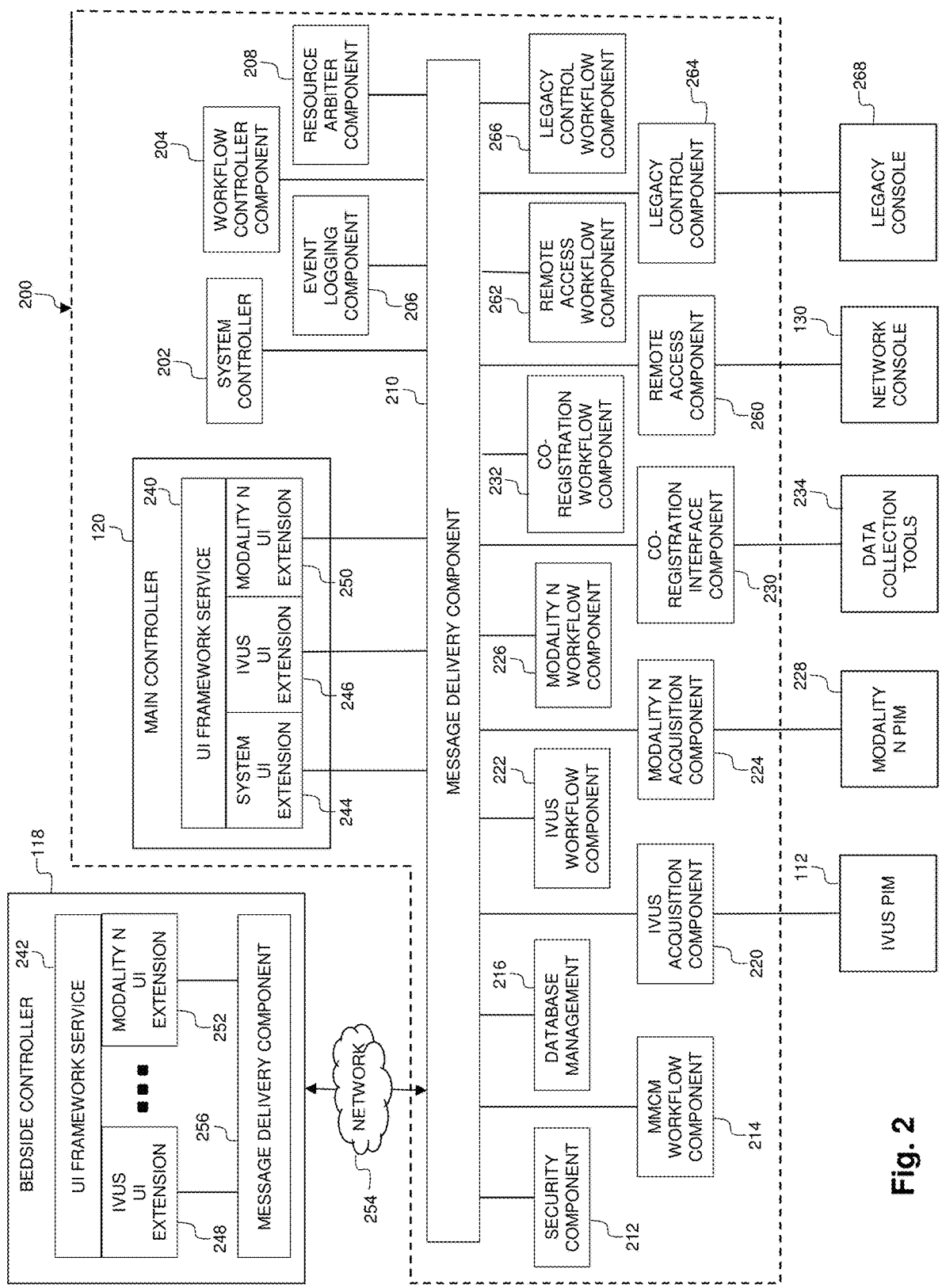
FIG. 2 is a functional block diagram of portions of the medical system of FIG. 1, including a processing framework executing on embodiments of the multi-modality processing system.

With reference now to FIG. 2, illustrated is a functional block diagram of portions of the medical system 100 of FIG. 1, including a processing framework 200 executing on an embodiment of the multi-modality processing system 101. The processing framework 200 includes various independent and dependent executable components that control the operation of the processing system 101, including the acquisition, processing, and display of multi-modality medical sensing data. In general, the processing framework 200 of processing system 101 is modular and extensible. That is, the framework 200 is comprised of independent software and/or hardware components (or extensions) respectively associated with different functions and medical sensing modalities. This modular design allows the framework to be extended to accommodate additional medical sensing modalities and functionality without impacting existing functionality or requiring changes to the underlying architecture. Further, an internal messaging system facilitates independent data communication between modules within the framework. In one instance, the processing framework 200 may be implemented as computer-executable instructions stored on a non-transitory computer-readable storage medium in the processing system 10. In other instances the processing framework 200 may be a combination of hardware and software modules executing within with the processing system 101.

Generally, in the embodiment shown in FIG. 2, processing framework 200 includes a plurality of components that are configured to receive medical sensing data from a plurality of medical sensing devices, process the data, and output the data as diagnostic images via the main controller 120, the bedside controller 118, or other graphical display device. The framework 200 includes several system-level components that manage the core system functions of the processing system 101 and also coordinate the plurality of modality-specific components. For instance, the framework 200 includes a system controller 202 that coordinates startup and shutdown of the plurality of executable components of the processing framework 200, including hardware and software modules related to acquisition and processing of patient diagnostic data. The system controller 202 is also configured to monitor the state of components executing within the framework 202, for instance, to determine if any components have unexpectedly stopped executing. In addition, the system controller 202 provides an interface through which other framework components may obtain system configuration and status information. Because the software framework 200 is modular, the system controller 202 is independent of the components within the framework that it manages so that errors and changes made to components do not affect the execution or structure of the system controller.

As mentioned above, the framework 200 is configured such that various extensions may be added and removed without system architecture changes. In certain embodiments, an extension executing within framework 200 may include a plurality of executable components that together implement the full functionality of the extension. In such embodiments, an extension may include an extension controller that is similar to the system controller 202 that is operable to startup, shutdown, and monitor the various executable components associated with the extension. For example, upon system startup, the system controller 202 may start an extension controller corresponding to a medical modality, and then the extension controller may, in turn, start the executable components associated with the modality. In one embodiment, extension controllers may be unallocated until system controller 202 associates them with a specific modality or other system task via parameters retrieved from a configuration mechanism, such as a configuration file.

The processing framework 200 further includes a workflow controller component 204 that is generally configured to govern the execution of the executable components of the framework 202 during multi-modality medical sensing workflows. The workflow controller component 204 may govern workflows executed by the processing framework 200 in various different manners.

The processing framework 200 further includes an event logging component 206 that is configured to log messages received from various components of the processing framework. For instance, during system startup, the system controller 202 may send messages about the status of components being started to the event logging component 206 which, in turn, writes the messages to a log file in a standardized format. Additionally, the processing framework 200 includes a resource arbiter component 208 that is configured to manage the sharing of limited system resources between various executable components of the framework 202 during multi-modality medical sensing and/or treatment workflows. For example, during a multi-modality workflow, two or more components associated with different modalities within the processing framework 202 may be vying for the same system resource such as a graphical display on the main controller 120. The resource arbiter component 208 may coordinate sharing of limited system resources in various manners such as through a lock system, a queue system, or a hierarchical collision management system.

In one embodiment, the system controller 202, workflow controller component 204, event logging component 206, and resource arbiter component 208 may be implemented as processor-executable software stored on non-transitory, computer-readable storage media, but in alternative embodiments, these components may be implemented as hardware components such as special purpose microprocessors, Field Programmable Gate Arrays (FPGAs), microcontrollers, graphics processing units (GPU), digital signal processors (DSP). Alternatively, the components of the processing framework may be implemented as a combination of hardware and software. In certain embodiments in which executable components are implemented in FPGAs, the system controller 202 may be configured to dynamically alter the programmable logic within the FPGAs to implement various functionality needed at the time. As an aspect of this, the processing system 101 may include one or more unassigned FPGAs that may be allocated by the system controller during system startup. For instance, if upon startup of the processing system 101, the system controller detects an OCT PIM and catheter coupled thereto, the system controller or an extension controller associated with OCT functionality may dynamically transform the programmable logic within one the unassigned FPGAs such that it includes functionality to receive and/or process OCT medical data.

To facilitate intersystem communication between different hardware and software components in the multi-modality processing system 101, the processing framework 200 further includes a message delivery component 210. In one embodiment, the message delivery component 210 is configured to receive messages from components within the framework 202, determine the intended target of the messages, and deliver the messages in timely manner (i.e., the message delivery component is an active participant in the delivery of messages). In such an embodiment, message metadata may be generated by the sending component that includes destination information, payload data (e.g., modality type, patient data, etc.), priority information, timing information, or other such information. In another embodiment, message delivery component 210 may be configured to receive messages from components within the framework 202, temporarily store the messages, and make the messages available for retrieval by other components within the framework (i.e., the message delivery component is a passive queue). In any case, the message delivery component 210 facilitates communication between executable components in the framework 200. For instance, the system controller 202 may utilize the message delivery component 210 to inquire into the status of components starting up during a system startup sequence, and then, upon the receiving status information, utilize the message delivery component to transmit the status information to the event logging component 206 so that it may be written to a log file. Similarly, the resource arbiter component 208 may utilize the message delivery component 210 to pass a resource token between components requesting access to limited resources.

In one example embodiment in which the message delivery component 210 is a passive queue, components in the framework 200 may packetize incoming medical sensing data into messages and then transmit the messages to a queue on the message delivery component where they may be retrieved by other components such as image data processing components. Further, in some embodiments, the message delivery component 210 is operable to make received messages available in a First-In-First-Out (FIFO) manner, wherein messages that arrive on the queue first will be removed from the queue first. In alternative embodiments, the message delivery component 210 may make messages available in a different manner for instance by a priority value stored in a message header. In one embodiment, the message delivery component 210 is implemented in random-access memory (RAM) in the processing system 101, but, in other embodiments, it may be implemented in non-volatile RAM (NVRAM), secondary storage (e.g., magnetic hard drives, flash memory, etc.), or network-based storage. Further, in one embodiment, messages stored on the message delivery component 210 may be accessed by software and hardware modules in processing system 101 using Direct Memory Access (DMA).

The processing framework 202 further includes a number of additional system components that provide core system functionality including a security component 212, a multi-modality case management (MMCM) component 214, and a database management component 216. In certain embodiments, the security component 212 is configured to provide various security services to the overall processing framework and to individual components. For example, components implementing an IVUS data acquisition workflow may utilize encryption application programming interfaces (APIs) exposed by the security component 212 to encrypt IVUS data before it is transmitted over a network connection. Further, the security component 212 may provide other security services, such as system-level authentication and authorization services to restrict access to the processing framework to credentialed users and also to prevent the execution of untrusted components within the extensible framework. The multi-modality case management (MMCM) component 214 is configured to coordinate and consolidate diagnostic data associated with a plurality of medical modalities into a unified patient record that may be more easily managed. Such a unified patient record may be more efficiently stored in a database and may be more amenable to data archival and retrieval. In that regard, the database management component 216 is configured to present transparent database services to the other components in the framework 200 such that database connection and management details are hidden from the other components. For example, in certain embodiments, the database management component 216 may expose an API that includes database storage and retrieval functionality to components of the framework 200. In other words, a medical sensing workflow component may be able to transmit diagnostic data to a local and/or remote database such as a DICOM or PACS server via the database component without being aware of database connection details. In other embodiments, the database management component 216 may be operable to perform additional and/or different database services such as data formatting services that prepare diagnostic data for database archival.

As mentioned above, the processing framework 200 of the multi-modality processing system 101 is operable to receive and process medical data associated with a plurality of modalities. In that regard, the processing framework 200 includes a plurality of modular acquisition components and workflow components that are respectively associated with different medical sensing and diagnostic modalities. For instance, as shown in the illustrated embodiment of FIG. 2, the processing framework 200 includes an IVUS acquisition component 220 and an IVUS workflow component 222 that are respectively configured to receive and process IVUS medical sensing data from the IVUS PIM 112. In accordance with the modular and extensible nature of the processing framework 200, any number of additional acquisition and workflow components may be independently added to the framework as denoted by the modality "N" acquisition component 224 and the modality "N" workflow component 226 that acquire and process data from a modality "N" PIM 228. For example, in certain embodiments, the processing system 101 may be communicatively coupled to the OCT PIM 114, the ECG system 116, a fractional flow reserve (FFR) PIM, a FLIVUS PIM, and an ICE PIM. In other embodiments, additional and/or different medical sensing, treatment, or diagnostic devices may be coupled to the processing system 101 via additional and/or different data communication connections known in the art. In such a scenario, in addition to the IVUS acquisition module 220, the processing framework 200 may include an FFR acquisition component to receive FFR data from an FFR PIM, a FLIVUS acquisition component to receive FLIVUS data from a FLIVUS PIM, an ICE acquisition component to receive ICE data from an ICE PIM, and an OCT acquisition component is operable to receive OCT data from an OCT PIM. In this context, medical data communicated between the executable components of the processing framework 200 and the communicatively coupled medical devices (e.g., PIMs, catheters, etc.) may include data collected by sensors, control signals, power levels, device feedback, and other medical data related to a sensing, treatment, or diagnostic procedure. Further, in certain embodiments, patient treatment devices may be communicatively coupled to the processing system 101 such as devices associated with radiofrequency ablation (RFA), cryotherapy, or atherectomy and any PIMs or other control equipment associated with such treatment procedures. In such an embodiment, the modality "N" acquisition component 224 and the modality "N" workflow component 226 may be configured to communicate with and control the treatment devices such as by relaying control signals, relaying power levels, receiving device feedback, and receiving data collected by sensors disposed on the treatment devices.

In one embodiment, once the acquisition components 220 and 224 have received data from connected medical sensing devices, the components packetize the data into messages to facilitate intersystem communication. Specifically, the components may be operable to create a plurality of messages from an incoming digital data stream, where each message contains a portion of the digitized medical sensing data and a header. The message header contains metadata associated with the medical sensing data contained within the message. Further, in some embodiments, the acquisition components 220 and 224 may be operable to manipulate the digitized medical sensing data in some way before it is transmitted to other portions of the framework 200. For example, the acquisition components may compress the sensing data to make intersystem communication more efficient, or normalize, scale or otherwise filter the data to aid later processing of the data. In some embodiments, this manipulation may be modality-specific. For example, the IVUS acquisition component 220 may identify and discard redundant IVUS data before it is passed on to save processing time in subsequent steps. The acquisition components 220 and 224 may additionally perform a number of tasks related to the acquisition of data including responding to interrupts generated by data buses (e.g., PCIe, USB), detecting which medical sensing devices are connected to processing system 101, retrieving information about connected medical sensing devices, storing sensing device-specific data, and allocating resources to the data buses. As mentioned above, the data acquisition components are independent from each other and may be installed or removed without disrupting data acquisition by other components. Additionally, acquisition components are independent of underlying data bus software layers (for example, through the use of APIs) and thus may be created by third parties to facilitate acquisition of data from third party medical sensing devices.

The workflow components of the processing framework, such as the IVUS workflow component 222, receive unprocessed medical sensing and/or diagnostic data from respective acquisition components via the message delivery component 210. In general, the workflow components are configured to control the acquisition of medical sensing data such as by starting and stopping data collection at calculated times, displaying acquired and processed patient data, and facilitating the analysis of acquired patient data by a clinician. As an aspect of this, the workflow components are operable to transform unprocessed medical data gathered from a patient into diagnostic images or other data formats that enable a clinician to evaluate a patient's condition. For example, an IVUS workflow component 222 may interpret IVUS data received from the IVUS PIM 112 and convert the data into human-readable IVUS images. In one embodiment, a software stack within the framework may expose a set of APIs with which the workflow component 222 and other workflow components in the framework may call to access system resources such as the computational resources, the message delivery component 210, and communication resources. After processing acquired data, the modality-centric workflow components may transmit one or more messages containing the processed data to other components within the framework 200 via the message delivery component 210. In some embodiments, before sending such messages, the components may insert a flag in the header indicating that the message contains processed data. Additionally, in some embodiments, after processing medical sensing data, the components may utilize the database management component 216 to transmit the processed data to archival systems such as a locally attached mass storage device or the network-based PACS server 127. In accordance with the modular architecture of the processing framework 200, the workflow components 222 and 226 are independent of each other and may be installed or removed without disrupting other components, and may be written by third parties. Further, due to their independence, they may be are operable to process signaling and imaging data from multiple medical sensing devices concurrently.

The processing framework 200 additionally includes a co-registration interface component 230 and a co-registration workflow component 232 that are configured to acquire and process data from any number of data collection tools 234 and co-register the acquired data with data acquired by one of the other acquisition components within the framework. In more detail, the co-registration interface component 230 may be operable to communicatively interface with medical data acquisition tools associated with any number of modalities, such as the ECG device 116 or the angiography system 117 of FIG. 1. In certain embodiments, the interface component 230 may be operable to standardize and/or transform incoming modality data such that it may be co-registered with other sensing data acquired by the processing system 101. As medical data is being acquired by the co-registration interface component 230, the co-registration workflow component 232 is configured to facilitate the co-registration of data from different modalities such as by spatially or temporally synchronizing data collection among medical sensing devices, aligning two or more acquired data sets based on spatial or temporal registration markers, and generating co-registered diagnostic images or other human-readable data that enable a clinician to evaluate a patient's condition. Further, in other embodiments, the co-registration workflow component 232 may be operable to spatially co-register catheter-gathered data in a two-dimensional (2-D) or three-dimensional (3-D) space using previously-generated 2-D images or 3-D models. For example, a catheter-based sensing tool may include fiducials that are tracked to generate position data during a sensing procedure, and the co-registration workflow component 232 may register this position data against previously acquired MRI data. Still further, the co-registration workflow component 232 may facilitate co-registration of multi-modality data acquired by native acquisition components within the framework 200 such as the IVUS acquisition component 220 and modality "N" acquisition component 224. Additionally, in some embodiments, a real-time clock may be integrated into the co-registration workflow component 232. U.S. Provisional Patent Application No. 61/473,591, entitled "DISTRIBUTED MEDICAL SENSING SYSTEM AND METHOD", discloses temporally synchronizing medical sensing data collection in more detail and is hereby incorporated by reference in its entirety.

As discussed above in association with FIG. 1, a clinician utilizing the processing system 101 may control workflows and view diagnostic images through the main controller 120 and the bedside controller 118. The main controller 120 and the bedside controller 118 respectively include user interface (UI) framework services 240 and 242 that support a plurality of user interface (UI) extensions (or components). In general, the UI extensions supported by the UI framework services 240 and 242 respectively correspond to medical sensing modalities and are operable to render a user interface for control of the associated acquisition workflow and display of processed sensing data. Similar to the processing framework 200, the UI frameworks 240 and 242 are extensible in that they support UI extensions that are independent of one another. That is, its modular design allows the UI frameworks 240 and 242 to be extended to accommodate additional medical sensing modality user interfaces without impacting existing user interfaces or requiring changes to the underlying UI architectures. In the illustrated embodiment, the main controller 120 includes a system UI extension 244 that renders a user interface containing core system controls and configuration options. For example, a clinician may startup, shutdown or otherwise manage the processing system 101 using the user interface rendered by the system UI extension 244. In one embodiment, the components of the main controller 120 may be considered part of the processing framework 200. The IVUS UI extensions 246 and 248 render user interfaces for the main controller 120 and bedside controller 118, respectively. For example, the IVUS UI extensions 246 and 248 may render and display the touch screen buttons used to control an IVUS workflow and also render and display the IVUS diagnostic images created by the IVUS workflow component 222. Similarly, the modality "N" UI extensions 250 and 252 render controls and images associated with a modality "N" workflow.

In one embodiment, the UI framework services 240 and 242 may expose APIs with which the UI extensions may call to access system resources such as a look-and-feel toolbox and error handling resources. Look-and-feel toolbox APIs enable the UI extensions to present a standardized user interface with common buttons, parallel workflow formats, and data presentation schemes for different modality workflows. In this manner, clinicians may more easily transition between acquisition modalities without additional user interface training. Further, co-registration UI extensions may present and/or combine processed image or signaling data from multiple modalities. For instance, a UI extension may display an electrocardiogram (ECG) wave adjacent to IVUS imaging data or may display an IVUS image overlaid with borders that were previously drawn on an OCT image. Further, in some embodiments, the UI framework services 240 and 242 may include a multi-tasking framework to coordinate concurrently executing UI extensions. For instance, in the event the processing system 101 is simultaneously acquiring data associated with more than one modality, the UI framework services 240 and 242 may present the user with a modality selector screen on which a desired user interface may be selected.

The UI framework service 240 communicates with the components of the processing framework 200 via the message delivery component 210. As shown in the illustrated embodiment of FIG. 2, the bedside controller 118 may be communicatively coupled to the processing framework 200 via a network connection 254. The network connection 254 may be any type of wired of wireless network connection such as an Ethernet connection or IEEE 802.11 Wi-Fi connection. Alternatively, one or both of the main and bedside controllers 120 and 118 may communicate with the processing framework 200 via a local bus connection such as a (PCIe) data bus connection, a USB connection, a Thunderbolt connection, a FireWire connection, or some other high-speed data bus connection. Further, in the illustrated embodiment of FIG. 2, the bedside controller includes a message delivery component 256 that is configured to facilitate message-based communication between the UI extensions in the bedside controller 118 and the components in the processing framework 200. In certain embodiments, the message delivery component 256 may extract diagnostic image data from network communication packets as they arrive over the network connection 254.

The processing framework 200 includes additional components that allow a clinician to access and/or control workflows executing in the multi-modality processing system 101. For example, the framework 200 includes a remote access component 260 that communicatively couples the network console 130 (FIG. 1) to the processing framework 200. In one embodiment, the remote access component 260 is operable to export control functionality of the processing system 101 to the network console 130, so that the network console may present workflow control functions in its user interface. In certain embodiments, the remote access component 260 may receive workflow commands from the network console 130 and forward them to a remote access workflow component 262. The remote access workflow component 262 may dictate the set of commands and diagnostic data to which a remote user may access through the network console 130. Further, the legacy control component 264 and legacy control workflow component 266 provide some level of access to modality workflow control and data to users of legacy consoles 268 (e.g. button consoles, mice, keyboards, standalone monitors).

In one embodiment, the core system components of the processing framework 200 and the additional components such as the modality-related components may be implemented as processor-executable software stored on non-transitory, computer-readable storage media, but in alternative embodiments, these components may be implemented as hardware components such as special purpose microprocessors, Field Programmable Gate Arrays (FPGAs), microcontrollers, graphics processing units (GPU), digital signal processors (DSP). Alternatively, the components of the processing framework may be implemented as a combination of hardware and software.

One of ordinary skill in the art will recognize that the processing framework 200 of FIG. 2 is simply an example embodiment and, in alternative embodiments, the framework may include different and/or additional components configured to carry out various medical sensing workflows. For instance, the processing framework 200 may further include executable components configured for the evaluation of a stenosis of a human blood vessel or configured to facilitate control of computer-assisted surgery or remotely-controlled surgery.

Figure 3:
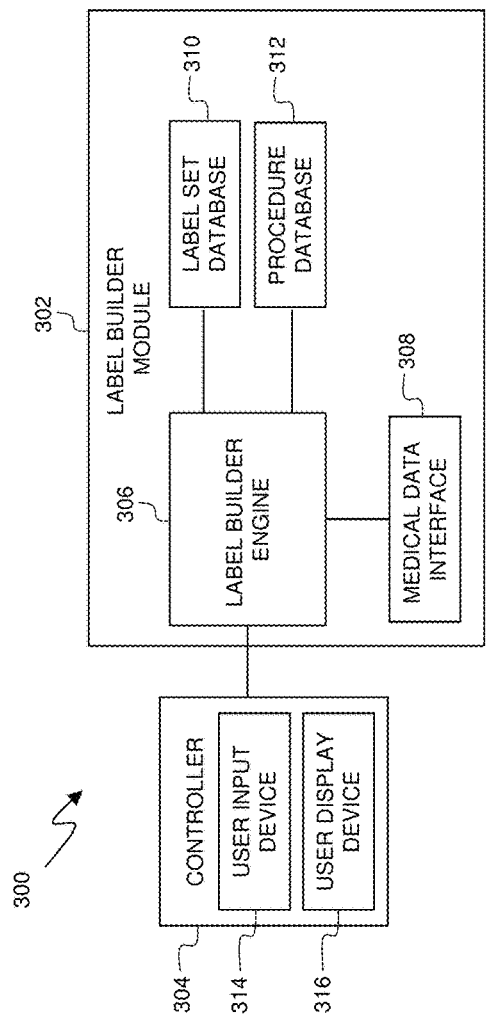
FIG. 3 is a functional block diagram of portions of the medical system of FIGS. 1 and 2, including a user interface component for labeling and/or indexing medical data according to some embodiments of the multi-modality processing system.

Referring now to FIG. 3, illustrated is a functional block diagram of portions of the medical system of FIGS. 1 and 2, including a user interface component 300 for labeling and/or indexing medical data according to some embodiments of the multi-modality processing system 100. In various embodiments, the user interface component 300 presents a nested list of indexes or labels used to identify medical data. The amount of data collected during a treatment or therapy can be substantial. The addition of multiple modalities only exacerbates the problem. Labeling and/or indexing relevant portions of the dataset facilitates review, searching, auditing, statistical analysis, and other uses of the data.

The user interface component 300 includes a label builder module 302 that constructs a relevant label based on user input and applies the label to a portion of medical data. The label builder module 302 contains one or more of a label builder engine 306, a medical data interface 308, a database of label sets 310, and a procedure database 312. The procedure database 312 contains information relevant to the procedure being performed such as an operative course of a procedure or treatment, a patient identification, patient vital statistics, a patient's medical history, and/or a status of the processing system 100. In some embodiments, the label set database 310 and/or the procedure database 312 is external to the label builder module 302, and thus the module 302 includes a database interface coupled to the respective database 310 or 312.

The user interface component also includes a controller 304, which itself includes a user input device 314 and a user display device 316. Examples of suitable user input devices 314 include, but are in no way limited to, keyboards, keypads, mice, trackballs, digital pens, touch-based interfaces, gesture-based interfaces, verbal and speech-recognition interfaces, adaptive interfaces, cameras, motion-sensing interfaces, and other user input devices known to one of skill in the art.

Portions of the user interface component 300 may be implemented, in whole or in part, as processor-executable software stored on non-transitory, computer-readable storage media and/or as hardware components such as special purpose microprocessors, FPGAs, microcontrollers, graphics processing units, and DSPs. In some embodiments, portions of the user interface component 300 are incorporated into components of the multi-modality processing system 100 described with reference to FIGS. 1 and 2. For example, in some such embodiments, controller 304 is a component of a bedside controller 118, a main controller 120, a boom display 122, and/or a network console 130 described with reference to FIG. 1. As a further example, in some such embodiments, the label builder module 302 is incorporated into a UI framework service 240 of a main controller 120, a UI framework service 242 of a bedside controller 118, and/or a UI extension such as IVUS UI extension 246 or IVUS UI extension 248 described with reference to FIG. 2. In other embodiments, the label builder module 302 is a separate and distinct component of the multi-modality processing system 100.

The label builder module 302 constructs a label to be applied to a unit of medical data such as a frame of an IVUS image, a segment of an OCT tomogram, a range of an FFR measurement, or other portion of a data set. In some embodiments, the label builder module 302 receives the medical data to be labeled via the medical data interface 308. In other embodiments, the label builder module 302 receives an identifier corresponding to the medical data either in addition to or as a substitute for receiving the medical data itself. For example, in one such embodiment, other components of the multi-modality processing system 100 separate from the label builder module 302 display the data on the user display device 316 without providing it to the label builder module 302. In another such embodiment, the medical data is distributed across a network.

The data to be labeled may be any suitable medical data collected by one or more of any modality implemented by the multi-modality processing system. In some embodiments, the medical data is unprocessed medical data and may be provided by a modality acquisition component (e.g., IVUS acquisition component 220 of FIG. 2, a forward-looking IVUS acquisition component, an FFR acquisition component, a CFR acquisition component, an OCT acquisition component, and/or a transesophageal echocardiography acquisition component). In some embodiments, the medical data is processed medical data and may be provided by a workflow component (e.g., IVUS workflow component 222 of FIG. 2, a forward-looking IVUS workflow component, an FFR workflow component, a CFR workflow component, an OCT workflow component, and/or a transesophageal echocardiography workflow component). In some embodiments, the medical data has been aggregated from multiple modalities and is provided by an MMCM workflow component 214 of FIG. 2.

To assemble a label, in some embodiments, the label builder engine 306 presents sets of possible labels, categorically arranged, on the user display device 316 for an operator to select. In various exemplary embodiments, sets of labels are derived from treatment or procedure names, locations within the body, anatomical structures such as vessel names or vessel segments, patient data, procedure data, and/or any other suitable identifier. In determining a set of labels to present, the label builder engine 306 may query the procedure database 312 to determine information pertaining to the current operating environment and/or the label set database 310 to determine labels that pertain to an operating environment. In one such embodiment, the label builder engines queries the procedure database 312 to determine an aspect of the current operating environment and subsequently queries the label set database 310 based on the aspect to determine pertinent labels. In some embodiments, the label builder engine 306 selects a set of labels based on the medical data or other corresponding medical data collected by another modality. As an example, a set of labels for IVUS data may include a label corresponding to blood pressure or pulse as measured by another sensor modality connected to the system 100. In that regard, data across modalities are coordinated using times stamps or other suitable techniques by the multi-modality processing system.

The label builder engine 306 presents the set of labels to the system operator via the user display device 316 of the controller 304. Using the user input device 314, the operator selects an appropriate label from the set. In some embodiments, the operator may supply an alternative label not contained in the set either in addition to or as a substitute for selecting a label from the set. The user selection is received at the label builder engine 306, and the corresponding label is stored. The label builder engine 306 may perform multiple iterations of assembling a set of labels, presenting the set, and receiving a selection. In some embodiments, a selected label determines the composition of subsequent label sets. In such embodiments, any iteration may depend on a response received in any previous iteration. For example, in one such embodiment, a parent set of labels is derived from vessel names and includes "LAD" (corresponding to "left anterior descending artery"), "LCX" (corresponding to "left circumflex artery"), and "RCA" (corresponding to "right coronary artery"). In the example, the operator selects "RCA" and the response is received at the label builder engine 306. Based on this response, the label builder engine 306 assembles a dependent set of labels based on the relevant segments of the corresponding right coronary artery. The label builder engine 306 then presents the dependent set of labels via the user display device 316.

In some embodiments, the label builder engine 306 supports multiple branching dependencies. In such embodiments, a label set may depend on any or none of the parent sets, and iterations may be added or removed based on previous responses.

Additionally, the label builder engine 306 may at any time receive a request via the user input device 314 to modify a previous response and repeat any dependent iterations. The label builder engine 306 may repeat the dependent iterations out of order and/or without repeating other intervening iterations. For example, a modification to a response relating to a second set of labels may cause a change to a fourth set of labels without necessarily causing a change to a first or third set of labels and thus without necessarily causing the first or third set of labels to be reiterated.

In embodiments that incorporate dependent sets of labels, a selected label is stored and a dependent set of labels is generated by the label builder engine 306. The generation of subsequent label sets including dependent sets may be substantially similar to that of the parent set. In that regard, subsequent sets may be populated by querying the label set database 310 and/or the procedure database 312. Subsequent sets of labels may be derived from treatment or procedure names, locations within the body, anatomical structures such as vessel names or vessel segments, patient data, procedure data, and/or any other suitable identifier. In some embodiments, the label builder engine 306 selects a subsequent set of labels based on the medical data or other corresponding medical data collected by another modality.

Similar to how subsequent sets may depend on labels selected from previous sets, in some embodiments, the label builder engine 306 may select and populate a set based on a label applied to another medical data set. For example, a first dataset may be labeled "POST" indicating that the data was collected after a certain point of a procedure. From this label, the label builder engine 306 may select label sets for subsequent data sets with the assumption that they were also collected after the critical point and are thus "POST."

In some embodiments, the label builder engine 306 preselects a label from a given set as a default selection. In such embodiments, the operator may be given the opportunity to override the preselected label. As an example, the label builder engine 306 may preselect the current time from a time-related label set. The operator may then have the ability to select an alternate time. Pre-selection may be based on system defaults, an operative course of a treatment, patient information, user preference, and/or other criteria.

When the final iteration is complete, the label builder engine 306 builds a final label based on the responses received. The final label may also include other relevant information obtained from sources other than user responses. This information may be retrieved from the procedure database 312 as well as from other sources and may include patient name or other patient identifier, patient statistics, operator name, a facility identifier, additional annotations, and/or other pertinent information. In some embodiments, the label includes data based on medical data provided by another modality of the system 100. For example, a label for imaging data may include a corresponding patient pulse rate or blood pressure.

The label builder engine 306 applies the final label to the medical data. In some embodiments, the label builder engine 306 modifies the medical data to add the label and returns the updated data for storage via the medical data interface 308. In other embodiments, the label builder engine 306 provides the label separate from and without modifying the corresponding medical data.

Figure 4:
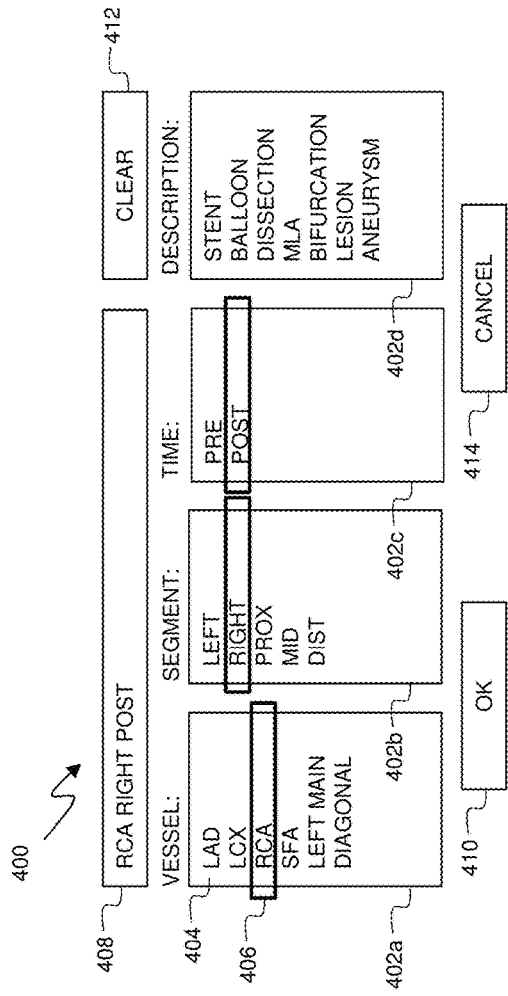
FIG. 4 is a diagram of an exemplary user interface for label construction according to some embodiments of the multi-modality processing system.

FIG. 4 is a diagram of an exemplary user interface 400 for label construction according to some embodiments of the multi-modality processing system 100. The user interface 400 may be displayed on a user display such as the user display 316 described with reference to FIG. 3. The user interface 400 represents one possible arrangement for displaying the information presented by the multi-modality processing system 100 and more specifically the label builder module 302 of the system. One skilled in the art will recognize that alternate arrangements are both contemplated and provided for.

In the illustrated embodiment, the user interface 400 includes four label set panes (panes 402a, 402b, 402c, and 402d), although other embodiments incorporate any number of panes. In some embodiments, the number of panes increases or decreases based on the labels selected. Each label set pane displays an associated label set, for example, label set 404, and provides both an area to select a label from the label set and an identifier 406 of the currently selected label. The interface 400 may also include a current selection pane 408 that displays one or more currently selected labels. In some embodiments, the current selection pane 408 allows an operator to select a label. For example, the pane 408 may allow typing or other use input. The user interface 400 may also contain one or more command elements for sending instructions to the label builder module 302. Exemplary instruction include select label, apply final label (i.e., OK button 410), clear currently selected labels (i.e., CLEAR button 412), and abort without applying a label (i.e., CANCEL button 414).

Figure 5:
FIG. 5 is a flow diagram of a method of determining and applying a label to medical data within a multi-modality processing system according to some embodiments of the present disclosure.

FIG. 5 is a flow diagram of a method 500 of determining and applying a label to medical data within a multi-modality processing system 100 according to some embodiments of the present disclosure. It is understood that additional steps can be provided before, during, and after the steps of method 500, and some of the steps described can be replaced or eliminated for other embodiments of the method.

In block 502, the medical data to be labeled is received by a module of the system 100 such as a label builder module 302 described with reference to FIG. 3. In some embodiments, an identifier corresponding to the medical data is received either in addition to or as a substitute for receiving the medical data itself. The identifier of the medical data may include some or all of the medical data and/or may include a pointer to data located elsewhere on the system or distributed across a network. In block 504, the module selects and populates a first set of labels. In some embodiments, this includes querying one or more databases such as a label set database 310 or a procedure database 312. In various exemplary embodiments, sets of labels are derived, in part or in whole, from treatment or procedure names, locations within the body, anatomical structures such as vessel names or vessel segments, patient data, procedure data, and/or any other suitable identifier. The sets of labels may also be derived, in part or in whole, from information pertaining to patient information, treatment regimen, statistical information, and any other contextual information. In some embodiments, the module selects a set of labels based on the medical data being labeled or other corresponding medical data collected by another modality. As an example, a set of labels for IVUS data may include a label corresponding to blood pressure or pulse as measured by another sensor modality connected to the system 100.

In block 506, the module presents the first set of labels at a display device such as the user display device 316 described with reference to FIG. 3. In block 508, the module receives a first label selection based on the first set of labels. The response may be entered via an input device such as the user input device 314 described with reference to FIG. 3. In some embodiments, the operator may supply an alternative label not contained in the first set either in addition to or as a substitute for selecting a label from the set. The operator-supplied label may be stored for future use such as reporting and inclusion in future label sets. The module receives the selection, and the selected label may be stored in the system 100. In block 510, a second set of labels may be generated by the label builder engine. The composition of subsequent sets, including the second set, may be substantially similar to that of the first set. In that regard, subsequent sets may be retrieved from a database and may be derived from treatment or procedure names, locations within the body, anatomical structures such as vessel names or vessel segments, patient data, procedure data, and/or any other suitable identifier. Subsequent sets may also be populated based on contextual information, which in turn, may be retrieve from a database. In some embodiments, the module selects a subsequent set of labels based on the medical data or other corresponding medical data collected by another modality.

Referring still to block 510, the module may also select and populate subsequent label sets (e.g., the second set) based on previously selected labels for the medical data. For example, in one such embodiment, the first set of labels is derived from vessel names and includes "LAD" (corresponding to "left anterior descending artery"), "LCX" (corresponding to "left circumflex artery"), and "RCA" (corresponding to "right coronary artery"). In the example, the operator selects "RCA" and the response is received. Based on this response, the second set of labels is populated based on the relevant segments of the corresponding right coronary artery.

The module may also select the second set based on labels previously selected for or applied to another medical data set. For example, a previous data set may have been labeled with a patient's name. In some embodiments, the module populates a second set to include the patient's name based on the label applied to the previous data.

In some embodiments, in block 512, a particular label or value from the second set of labels is preselected. The particular label may be preselected based on any suitable criteria such as a system default, a customary flow of a treatment, patient information, and/or other criteria. As an example, in some embodiments, a time stamp from data acquisition is preselected from a time-related label set.

In block 514, the second set of labels is presented at the display device. In block 516, the module receives a second label selection from a user based on the second set of labels. The response may be entered via the input device such as the user input device 314 described with reference to FIG. 3. In some embodiments, the second label selection replaces a preselected label or value.

In block 518, it is determined whether the label query is complete. If not, subsequent iterations of assembling a set of labels, presenting the set, and receiving a selection may be performed in block 520. Any iteration may depend on a response received in any previous iteration. Of course, any iteration may be independent of any or all previous iterations. At any time, a request may be received via the input device to modify a previous response and repeat any dependent iteration. Dependent iterations may be performed out of order and/or without repeating other intervening iterations. For example, a modification to a response relating to a second set of labels may cause a change to a fourth set of labels without necessarily causing a change to a first or third set of labels and thus without necessarily causing the first or third set of labels to be reiterated.

When the label query is complete, in block 522, the final label is assembled from the responses received. The final label may also include other relevant information obtained from sources other than user responses such as patient name or other patient identifier, patient statistics, operator name, a facility identifier, additional annotations, and/or other pertinent information. In some embodiments, the label includes data based on medical data provided by another modality. For example, a label for imaging data may include a corresponding patient pulse rate or blood pressure.

In block 524, the final label is applied to the medical data. In some embodiments, the medical data is modified to add the label and the updated data is then stored and/or displayed. In other embodiments, the label is separate from the corresponding medical data, and no modification of the data is performed.

The systems and methods of the present disclosure provide a mechanism for selecting and assigning labels to medical data across modalities. Assigning labels to medical data may greatly improve data handling including searching and retrieval. In some embodiments, the assigned labels determine which portions of the medical data are stored, retained, and/or archived. For example, in an embodiment, unlabeled data is discarded after a certain time has elapsed, while labeled data is retained. This allows important data to be preserved and avoids storing redundant data. In another embodiment, labeled data is uploaded to another data processing system for further analysis. In another embodiment, a data processing system requests medical data labeled with one or more key terms. To further facilitate retrieval, in some embodiments, a searchable index of medical data is created from the assigned labels for fast and effective retrieval. By providing lists of possible labels, some embodiments encourage the use of standardized terms while still allowing operators to select terms outside of the list to cover special cases. To avoid overwhelming operators, some embodiments refine the list according to previous selections, procedure information, patient information, other medical data, and/or other criteria. This allows operators to see the most relevant labels, and thereby improves labeling speed and accuracy. Of course, it is understood that these advantages are merely exemplary, and no particular advantage is required for any particular embodiment.

Figure 6:
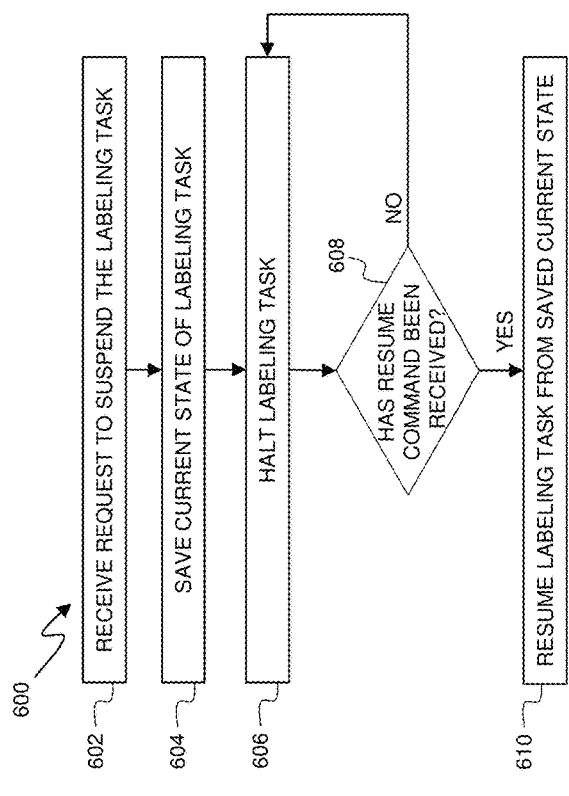
FIG. 6 is a flow diagram of a method of handling an interrupt to a labeling procedure within a multi-modality processing system according to some embodiments of the present disclosure.

FIG. 6 is a flow diagram of a method 600 of handling an interrupt to a labeling procedure within a multi-modality processing system 100 according to some embodiments of the present disclosure. In some embodiments, the labeling procedure supports interrupt commands such as suspend or halt. A user may suspend the labeling procedure while other tasks are performed. For example, a window used to display label sets may be minimized or hidden while underlying windows are viewed. In another example, a modality connected to the processing system 100 issues an interrupt as part of an error procedure that causes labeling to be suspended. When the system or user is ready to continue, the labeling procedure may be resumed from a previous state.

In block 602, a request is received to suspend the labeling task. The request may be issued by a user, by a component of the multi-modality system 100, by an external device or system including modalities coupled to the multi-modality system 100 and computing devices networked systems to the system 100, or by any other suitable source. In some embodiments, it is determined whether the source of the request has permission to suspend the labeling task. In block 604, the current state of the labeling task is saved. In block 606, the labeling task is halted. In block 608, it is determined whether a resume command has been received. If not, the labeling task remains halted in block 606. When the resume request is received, the labeling task is resumed in block 610. By providing a mechanism for a safe interruption of the labeling task, the method allows operators to attend to higher-priority matters without loss of data.

Figure 7:
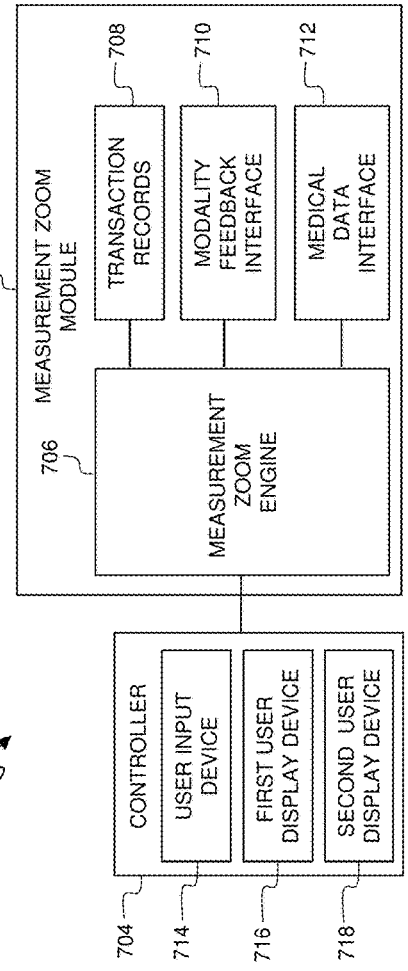
FIG. 7 is a functional block diagram of portions of the medical system of FIGS. 1 and 2, including a user interface component for performing on-demand enhancement of medical data according to some embodiments of the multi-modality processing system.

Referring now to FIG. 7, illustrated is a functional block diagram of portions of the medical system of FIGS. 1 and 2, including a user interface component 700 for performing on-demand enhancement of medical data according to some embodiments of the multi-modality processing system 100. Examples of enhancements include zooming, adjusting brightness, adjusting opacity, adjusting a color mask, increasing and decreasing resolution, resampling, interpolating, adjusting gain, and measuring including measuring distance, area, volume, and rate of change. Further enhancements combine data collected by multiple modalities and refine processing parameters applied to the medical data. Yet further exemplary enhancements perform 3d reconstruction. Enhancements may also include labeling, highlighting, or annotating a portion of the medical data, such as the labeling described with respect to FIGS. 3-6. Other enhancements are contemplated and provided for. Such multi-modality enhancements assist operators in navigating through the wealth of data and in drawing meaningful and accurate diagnostic correlations. In some embodiments, the user interface component 700 performs measurement determinations based on received location markers. The interface component 700 allows operators to specify points to highlight, mark, and/or measure. This gives the operator a context for the images and data on display, linking the patient to the data.

The user interface component 700 includes a measurement zoom module 702 coupled to a controller 704 or operator interface. The measurement zoom module 702 contains one or more of a measurement zoom engine 706, a memory device for storing a transaction record 708, a modality feedback interface 710, and a medical data interface 712. The controller 704 includes a user input device 714 and one or more user display devices (illustrated as a first user display device 716 and a second user display device 718). The user input device 714 may be substantially similar to the user input device 314 described with respect to FIG. 3. In that regard, examples of suitable user input devices 714 include, but are in no way limited to, keyboards, keypads, mice, trackballs, digital pens, touch-based interfaces, gesture-based interfaces, verbal and speech-recognition interfaces, adaptive interfaces, cameras, motion-sensing interfaces, and other user input devices known to one of skill in the art.

Portions of the user interface component 700 may be implemented, in whole or in part, as processor-executable software stored on non-transitory, computer-readable storage media and/or as hardware components such as special purpose microprocessors, FPGAs, microcontrollers, graphics processing units, and DSPs. In some embodiments, portions of the user interface component 700 are incorporated into components of the multi-modality processing system 100 described with reference to FIGS. 1 and 2. For example, in some such embodiments, controller 704 is a component of a bedside controller 118, a main controller 120, a boom display 122, and/or a network console 130 described with reference to FIG. 1. As a further example, in some such embodiments, the measurement zoom module 702 is incorporated into a UI framework service 240 of a main controller 120, a UI framework service 242 of a bedside controller 118, and/or a UI extension such as IVUS UI extension 246 or IVUS UI extension 248 described with reference to FIG. 2. In other embodiments, the measurement zoom module 702 is a separate and distinct component of the multi-modality processing system 100.

In some embodiments, the measurement zoom module 702 performs an on-demand enhancement of medical data. Examples of suitable enhancements include zooming, adjusting brightness, adjusting opacity, adjusting a color mask, increasing and decreasing resolution, resampling, interpolating, adjusting gain, and measuring including measuring distance, area, volume, and rate of change. Enhancements may also include labeling or annotating a portion of the medical data, such as the labeling described with respect to FIGS. 3-6. Other enhancements are both contemplated and provided for. The measurement zoom module 702 first receives a reference set of medical data via the medical data interface 712. In some embodiments, an identifier corresponding to the medical data is received either in addition to or as a substitute for receiving the medical data itself. The identifier of the medical data may include some or all of the medical data and/or may include a pointer to data located elsewhere on the system or distributed across a network. The reference data may also be displayed on a display device of the controller 704 (e.g., the first user display device 716) for the operator to view. The control of the display and the data handling may be performed by the measurement zoom module 702 directly, and/or by other components of the multi-modality processing system 100 separate from the measurement zoom module 702.

The reference data may be any suitable medical data. In some embodiments, the medical data includes unprocessed medical data and may be provided by a modality acquisition component (e.g., IVUS acquisition component 220 of FIG. 2, a forward-looking IVUS acquisition component, an FFR acquisition component, a CFR acquisition component, an OCT acquisition component, and/or a transesophageal echocardiography acquisition component). In some embodiments, the medical data includes processed medical data and may be provided by a workflow component (e.g., IVUS workflow component 222 of FIG. 2, a forward-looking IVUS workflow component, an FFR workflow component, a CFR workflow component, an OCT workflow component, and/or a transesophageal echocardiography workflow component). In some embodiments, the medical data includes data aggregated from multiple modalities and may be provided by a multi-modality component.

The measurement zoom module 702 may receive a region identifier suitable for determining a data set or a portion of a data set to enhance. In various embodiments, the region identifier takes the form of a set of bounding coordinates, a label, a measurement, and/or a bookmarked location. The measurement zoom module 702 receives the region identifier from the user input device 714 and/or from another system component such as a modality workflow component. For example, in an exemplary embodiment, the measurement zoom module 702 receives an identifier of a region to enhance from an IVUS workflow component 222 via the modality feedback interface 710. In the embodiment, the region identifier is configured to highlight, display, or otherwise draw attention to an area of interest detected by the workflow component. For example, an area of interest may be a vessel wall, a stent, and/or a characterized tissue such as a plaque or lesion. Such automated enhancements allow components of the system to alert the operator to potentially important data that might otherwise go unnoticed.

In some embodiments, the region identifier is converted from an initial format. For example, the region identifier may include a set of rectangular coordinates corresponding to pixels of the first display device 716, whereas the reference data may be represented in polar coordinates on a different scale. Accordingly, in various embodiments, the measurement zoom engine 706 of the module 702 converts the region identifier from the initial format into an appropriate data format. This may include one or more of scale conversion, coordinate conversion, shape translation, and other suitable conversions known to one of skill in the art.

The measurement zoom module 702 may also receive an enhancement selection that specifies one or more enhancement functions to perform. The enhancement selection may be received from the user input device 714 and/or another component of the system via the modality feedback interface 710.

Based on one or more of the enhancement selection, the region identifier, and the reference data, the measurement zoom engine 706 determines a target data set for the enhancement. The target data set includes a portion of the reference data used to specify the region in some instances. The target data set may also include alternate data sets either in addition to the reference data set or instead of the reference data set. In such embodiments, the data sets included in the target set may correspond to different modalities, a single modality at different times, a single modality in different operating modes, as well as other combinations of modalities and operating conditions. In performing some enhancements, the measurement zoom engine 706 may directly or indirectly combine data sets to form the reference data set. Accordingly, in one embodiment, the measurement zoom engine 706 provides a command at the modality feedback interface 710 that instructs an MMCM component to combine at least portions of data sets collected by two or more modalities. In a related embodiment, the measurement zoom engine 706 receives data sets collected by the two or more modalities and performs the combination within the engine 706. Similarly, in performing some enhancements, the measurement zoom engine 706 may cull data sets in order to improve responsiveness and reduce the burden on storage, networking, and/or processing resources. In one such embodiment, the measurement zoom engine 706 culls data outside the region identifier.

In some embodiments, a particular enhancement involves the collection of data. The measurement zoom engine may directly or indirectly collect additional data sets to add to the target data set. For example, the measurement zoom engine 706 may issue a command via the modality feedback interface 710 that instructs the multi-modality processing system to collect data from an attached instrument and capture a subsequent data set. The subsequent data set may correspond to the same modality as the reference data set, may correspond to one or more different modalities, and/or may correspond to a combination of modalities that includes the modality of the reference data set. In this way, the measurement zoom engine 706 is capable of both enhancing existing data and guiding the collection of subsequent data.

Once the target data set is identified, the measurement zoom engine 706 may perform the enhancement on the target data. Some examples of enhancements include zooming, adjusting brightness, adjusting opacity, adjusting a color mask, increasing and decreasing resolution, resampling, interpolating, adjusting gain, and measuring including measuring distance, area, volume, and rate of change. As a further example, in some embodiments, the measurement zoom engine 706 modifies one or more processing parameters applied to the target data. In some embodiments, the measurement zoom engine 706 applies modified parameters to the data directly. In some embodiments, the measurement zoom engine 706 applies modified parameters to the data indirectly by feeding back modifications at the modality feedback interface 710 for use by the appropriate system component. In some embodiments, the engine 706 applies the modified parameters directly and indirectly. In one exemplary embodiment, the measurement zoom engine 706 indirectly modifies a focal distance parameter used by an IVUS workflow component (e.g., IVUS workflow component 222 of FIG. 2) to create focused IVUS data. In so doing, the measurement zoom engine 706 provides a command at the modality feedback interface 710 that instructs the workflow component 222 to modify the focal distance parameter in order to provide increased data granularity and resolution within a region corresponding to the region identifier. In a further exemplary embodiment, the measurement zoom engine 706 provides a command at the modality feedback interface 710 that instructs the IVUS workflow component to change operating mode and perform a power flow analysis (e.g., Chromaflo® imaging, a trademark of Volcano Corporation) within the region corresponding to the region identifier.

In some embodiments, the reference data and the enhanced target data are displayed on different user display devices (e.g., first user display device 716 and second user display device 718, respectively). In some embodiments, these display devices correspond to a single physical display device at different points in time. Thus, the reference data set may be displayed on a monitor at a first point in time, and the enhanced data may be displayed on the monitor at a later time. In some embodiments, these display devices correspond to portions of a single display environment shown on a single monitor or display using representations such as "windows" of a display "desktop" or regions of a display workspace. In some embodiments, the first and second display devices correspond to first and second separate physical displays (e.g., first and second monitors, respectively). Displaying the reference data and the enhanced target data on different user display devices may be especially helpful in applications where user input may obscure part of a display, such as in touchscreen applications.

The measurement zoom module 702 may also provide an interface for storing a transaction record. A transaction record may include a region identifier, an enhancement selection, a data set identifier, a portion of the reference data set, a portion of the enhanced target data set, a modified processing parameter, and/or other suitable elements of the transaction. The transaction record may be stored within the transaction records database 708 or provided at the medical data interface 712 for transmission and/or storage by components of the system such as the database management component 216 described with respect to FIG. 2. In some embodiments, the transaction record includes a bookmark that records an aspect of the enhancement operation including a description of a data set, a region, an enhancement, and/or another parameter. The bookmark can be retrieved and used to restore a previous state and to apply previous data sets, region selections, enhancements, and/or parameters to subsequent data sets. The bookmark may serve as a label for indexing as described above with respect to FIGS. 3-6 or may include such a label.

The measurement zoom module 702 may also perform on-demand measurement designed to provide additional detail and thereby facilitate diagnostic analysis. For example, an operator can request a detailed measurement at a particular point, referred to as a pinpoint measurement. In such an example, the measurement zoom module 702 receives a location marker designating the point and performs an analysis of the available medical data to determine the requested measurement. The analysis may include data interpolation, predictive analysis, the cross-referencing of medical data sets across modalities, and/or other forms of data analysis. In another example, an operator can request a measurement between two or more reference points. In such an example, the measurement zoom module 702 receives the reference points and performs a measurement such as a distance measurement, a volume measurement, an area measurement, a time measurement, a rate of change measurement, and/or other suitable measurements in relation to the reference points. These measurements are merely exemplary, and other types of measurements are both contemplated or provided for.

As disclosed above, a reference data set may be displayed on a user display device (e.g., first user display device 716). The measurement zoom module 702 receives one or more location markers based on the reference data. In various embodiments, the location markers are received from a user input device (e.g., the user input device 714 of FIG. 7) and/or a component of the multi-modality processing system. For example, a workflow component of the multi-modality system 100 may specify a location marker to alert the operator to relevant diagnostic features or areas of interest such as a vessel wall, a stent, a plaque, a lesion, other characterized tissue, and/or other structures of interest. In some embodiments, a location marker is determined by a combination of user input and system component feedback. For example, a user may specify a first location that is adjusted or snapped to a nearby point of interest identified by a component or module of the multi-modality processing system.

The measurement zoom module 702 may also receive a measurement selection from a user input device and/or a component of the multi-modality processing system. The measurement selection may correspond to one or more measurement functions such as a distance measurement, an area measurement, a volume measurement, a time measurement, a rate of change measurement, and/or other suitable measurements in relation to the reference points.

Based on the one or more location markers, the measurement selection, and/or the reference data set, the measurement zoom engine 706 identifies a target data set to measure. In some embodiments, the target data set includes a portion of the reference data set. The target data set may also include other data sets either in addition to the reference data set or instead of the reference data set. In such embodiments, the data sets included in the target set may correspond to different modalities, a single modality at different times, a single modality in different operating modes, as well as other combinations of modalities and operating conditions.

Once the target data is identified, the measurement zoom engine 706 performs the measurement or measurements corresponding to the measurement selection. In an exemplary embodiment, the measurement selection specifies a distance measurement. In the example, the engine 706 determines a pixel distance between the location markers and converts the pixel distance to a physical distance between the corresponding points, although other methods of determining a distance measurement are contemplated and provided for. In doing so, the measurement zoom engine 706 may perform a conversion from a first format relative to the user display device (e.g., pixel-based increments) to a second format relative to a physical distance (e.g., millimeter-based increments) and may perform a conversion from a first coordinate system (e.g., polar coordinates) into a second coordinate system (e.g., Cartesian coordinates). Accordingly, the measurement zoom engine 706 may receive a conversion factor via the modality feedback interface 710 based on an operating parameter of the associated modality. Continuing the exemplary embodiment, the measurement zoom engine 706 receives a conversion factor of samples per millimeter and receives a conversion factor of samples per pixel. From this, the measurement zoom engine 706 determines a number of pixels per millimeter.

As previously described, in some embodiments, the system includes multiple displays. Accordingly, the reference data, the target data, the location markers, and the measured value may be displayed on any one or more of the display devices. In one such embodiment, reference data is displayed on the first user display device 716. An operator enters the location markers by a touch sensor (a type of user input device 714) overlaying the first user display device 716. The measurement zoom engine 706 updates the first user display device 716 with icons illustrating the location markers and the measured value and also updates a second user display device 718 with icons illustrating the location markers and the measured value. Displaying location markers and measured values on multiple user display devices is especially helpful in applications where user input may obscure part of a display such as touchscreen applications.

In some implementations, the measurement zoom module 702 provides an interface for storing elements of a measurement operation such as location markers and measured values. For example, the measurement zoom engine 706 may store or provide for storing a transaction record, which may include information regarding a location marker, a measurement selection, a measured value, a portion of the reference data set, a portion of the target data set, and/or other suitable elements of the transaction. The transaction record may be stored within the transaction records database 708 or provided at the medical data interface 712 for transmission and/or storage by components of the system such as the database management component 216 described with respect to FIG. 2. In some embodiments, the transaction record includes a bookmark that records an aspect of the measurement operation including a description of a data set, a location marker, a measurement type, a measured value, or another parameter. The bookmark can be retrieved and used to restore a previous state and to apply previous data sets, location markers, measurement types, and/or other parameters to subsequent data sets. The bookmark may serve as a label for indexing as described above with respect to FIGS. 3-6 or may include such a label.

Figure 8:
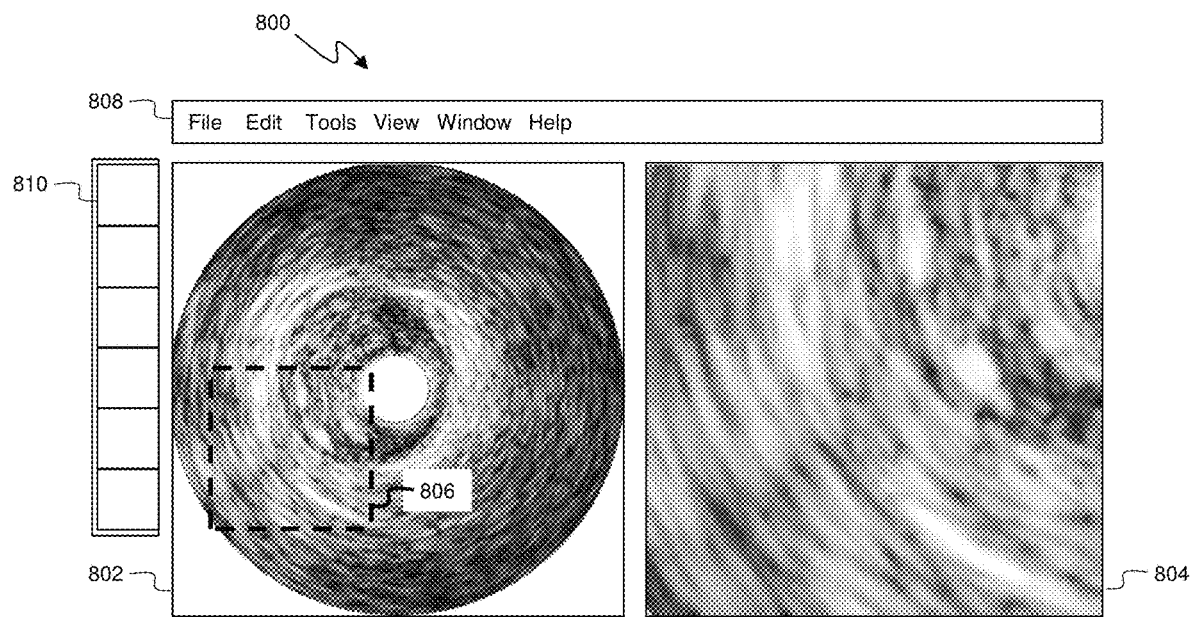
FIG. 8 is a diagram of an exemplary user interface for on-demand data enhancement according to some embodiments of the multi-modality processing system.

FIG. 8 is a diagram of an exemplary user interface 800 for on-demand data enhancement according to some embodiments of the multi-modality processing system 100. The user interface 800 may be presented on a single user display or multiple displays such as the first and second user displays 716 and 718 described with reference to FIG. 7. The user interface 800 represents one possible arrangement for displaying the information presented by the multi-modality processing system and more specifically the measurement zoom module 702 of the system. One skilled in the art will recognize that alternate arrangements are both contemplated and provided for.

The interface 800 included a first data display window 802 and a second data display window 804, which may correspond to different display devices, a single physical display device at different points in time, different portions of a single display environment on a single display device (using representations such as "windows" of a display "desktop" or regions of a display workspace), and/or different physical displays (i.e., different monitors). In the illustrated embodiment, the first data display window 802 presents a reference data set in a first window of a desktop and the second data display window 804 presents an enhanced target data set in a second window of the desktop.

The interface 800 may also include a region selection tool 806 that enables an operator to specify a region or data portion. In various non-limiting examples, the operator can specify a region using typed coordinates, using reference points designated by mouse input, touch-based input, or digital pen input, using geometric shapes designated by mouse input, touch-based input, or digital pen input, and/or other methods of data entry. In that regard, the region selection tool 806 allows an operator to select a region or data portion by parsing the provided user input.

The interface may also include a toolbar 808. In various embodiments, the toolbar 808 is used to select commands for the multi-modality processing system. Exemplary commands include selection of a region to enhance, selection of an enhancement to perform, as well as data store and load commands. The interface may also include a number of command elements 810 for quickly selecting commands to send to the multi-modality processing system. Any command that may be selected from a toolbar is suitable for selection using a command element 810. In that regard, in an exemplary embodiment, the interface 800 includes command elements 810 configured to select an enhancement to perform.

Figure 9:
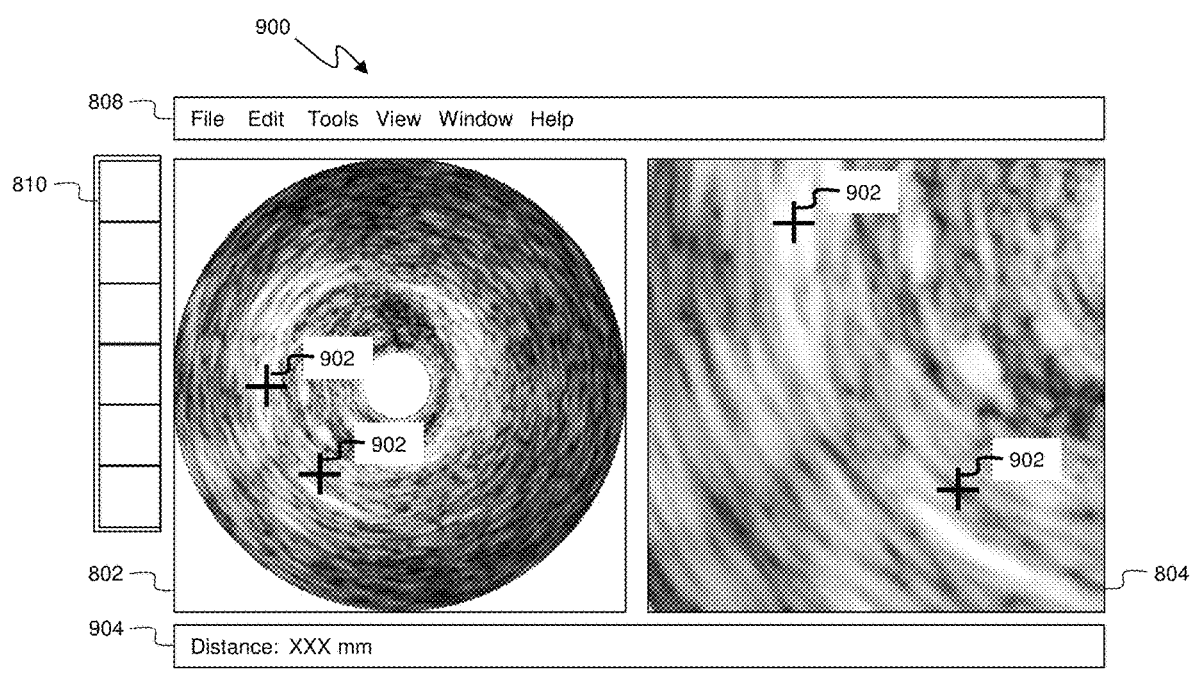
FIG. 9 is a diagram of an exemplary user interface for data measurement according to some embodiments of the multi-modality processing system.

FIG. 9 is a diagram of an exemplary user interface 900 for data measurement according to some embodiments of the multi-modality processing system 100. The user interface 900 may be presented on a single user display or multiple displays such as the first and second user displays 716 and 718 described with reference to FIG. 7. The user interface 900 represents one possible arrangement for displaying the information presented by the multi-modality processing system and more specifically the measurement zoom module 702 of the system. One skilled in the art will recognize that alternate arrangements are both contemplated and provided for.

In many respects, user interface 900 is substantially similar to user interface 800 of FIG. 8. In that regard, user interface 900 may include a first data display window 802 and a second data display window 804 corresponding to different display devices, a single physical display device at different points in time, different portions of a single display environment of a single display device (using representations such as "windows" of a display "desktop" or regions of a display workspace), and/or different physical displays (i.e., different monitors). User interface 900 may also include a toolbar 808 and command elements 810. User interface 900 may also include markers 902, icons that correspond to location markers provided to the system for use in data measurement. The location markers may be provided by the operator via the user input device 1212. In some embodiments, the operator designates and provide location markers using typed coordinates, using a mouse input, using a touch-based input, and/or using digital pen input. The location markers may also be provided by another component of the system 100 via the module interface 1208 either in addition to or instead of the operator-provided location markers. While two location markers are illustrated, in other embodiments, any number of location markers may be provided. In the illustrated embodiment, the markers 902 are displayed in the first data display window 802 and the second data display window 804, although further embodiments display the markers in the first data display window 802 or the second data display window 804. The user interface may also include a measurement output region 904 that displays measurement values determined based on the location markers. In some embodiments, the measurement values are displayed in one or more of the first data display window 802 and the second data display window 804 in addition to or in lieu of the measurement output region 904. While the illustrated measurement output region 904 displays a distance, in other embodiments, the measurement output region 904 can display any type of measurement utilized by the system including an area measurement, a volume measurement, a time measurement, a rate of change measurement, and/or other suitable measurements in relation to the reference points.

Figure 10:
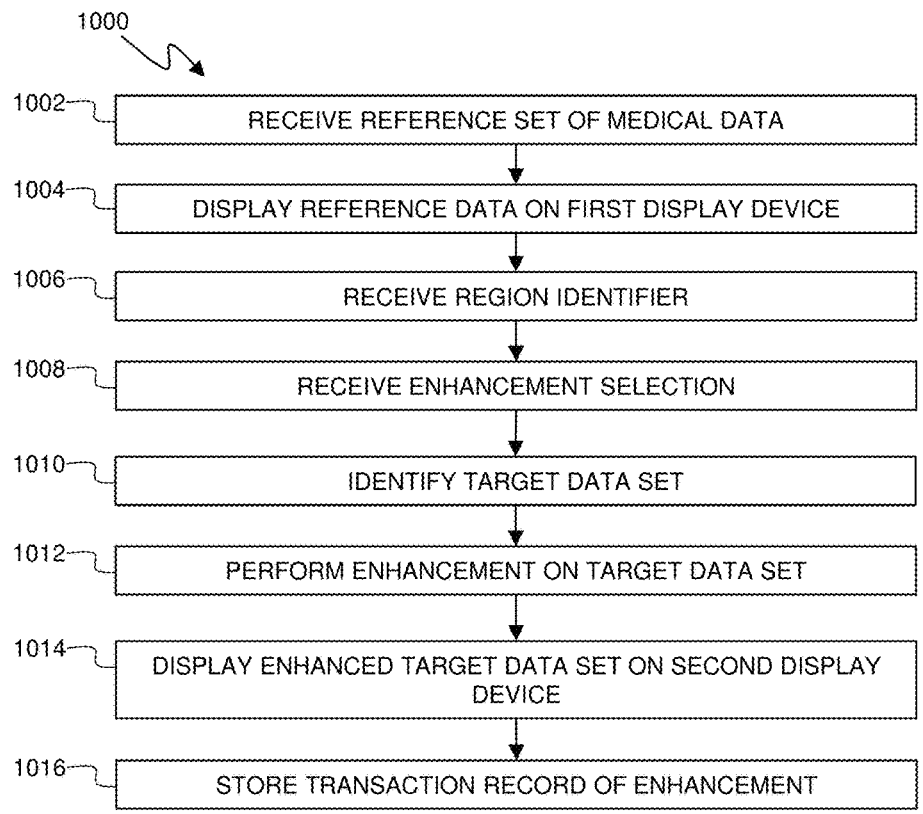
FIG. 10 is a flow diagram of a method of on-demand data enhancement within a multi-modality processing system according to some embodiments of the present disclosure.

FIG. 10 is a flow diagram of a method 1000 of on-demand data enhancement within a multi-modality processing system 100 according to some embodiments of the present disclosure. It is understood that additional steps can be provided before, during, and after the steps of method 1000, and some of the steps described can be replaced or eliminated for other embodiments of the method.

In block 1002, a reference set of medical data is received by the multi-modality processing system 100. In some embodiments, an identifier corresponding to the medical data is received either in addition to or as a substitute for receiving the medical data itself. The identifier of the medical data may include some or all of the medical data and/or may include a pointer to data located elsewhere on the system or distributed across a network. The reference set of medical data may be any suitable medical data. For example, the medical data may include unprocessed medical data provided by a modality acquisition component, processed medical data provided by a workflow component, and/or aggregate data corresponding to multiple modalities and provided by a multi-modality component. In block 1004, the reference set of medical data may be displayed on a first display device.

In block 1006, a region identifier is received. The region identifier corresponds to a subset of the reference set of medical data. In various embodiments, the region identifier takes the form of a set of bounding coordinates, a region identifier such as a grid index, a gesture, a command, a label, a measurement, a bookmarked location, and/or other suitable format. In some embodiments, the region identifier is received from a user input device such as user input device 714 described with reference to FIG. 7. Examples of suitable user input devices include, but are not limited to, keyboards, keypads, mice, trackballs, digital pens, touch-based interfaces, gesture-based interfaces, verbal and speech-recognition interfaces, adaptive interfaces, cameras, motion-sensing interfaces, light-based sensing mechanisms (e.g., infrared sensing), and other user input devices known to one of skill in the art. In some embodiments, the region identifier is received from another system component such as a modality workflow component. In one such embodiment, the region identifier is configured to highlight, display, or otherwise draw attention to a structure of interest. Such automated enhancements allow components of the system to alert the operator to potentially important data that might otherwise go unnoticed.

In some embodiments, the region identifier is converted from an initial format. For example, the region identifier may include a set of rectangular coordinates corresponding to pixels of a display device, whereas the reference data may be represented in polar coordinates on a different scale. Accordingly, in various embodiments, the region identifier is converted from the initial format into an appropriate data format. This may include one or more of scale conversion, coordinate conversion, shape translation, and other suitable conversions known to one of skill in the art.

In block 1008, an enhancement selection is received. The selection identifies one or more operations to perform and is received from a user input device and/or a component of the system.

In block 1010, a target data set is identified based on one or more of the enhancement selection, the region identifier, and the reference data. In some embodiments, the target data set includes a portion of the reference data set. The target data set may also include alternate data sets either in addition to the reference data set or instead of the reference data set. In such embodiments, the data sets included in the target set may correspond to different modalities, a single modality at different times, a single modality in different operating modes, as well as other combinations of modalities and operating conditions. In some embodiments, the method includes directly or indirectly combining data sets to form the target data set. Likewise, in some embodiments the method includes culling portions of the target data set. In one such embodiment, the method includes culling data outside a region corresponding to the region identifier.

In block 1012, an enhancement is performed on the target data set by the system 100. In various embodiments, the enhancement is determined by the enhancement selection, the region identifier, and/or the target data set. Examples of enhancements include zooming, adjusting brightness, adjusting opacity, adjusting a color mask, increasing and decreasing resolution, resampling, interpolating, adjusting gain, and measuring including measuring distance, area, volume, and rate of change. Further enhancements combine data collected by multiple modalities and refine processing parameters applied to the medical data. For example, in one such embodiment, the multi-modality processing system 100 modifies a focal range parameter applied by an IVUS workflow component of the system 100 in order to provide increased resolution within the region specified by the region identifier. In another such embodiment, the multi-modality processing system modifies a mode of operation of a workflow component of the system 100.

Enhancements may also include labeling or annotating a portion of the medical data, such as the labeling described with respect to FIGS. 3-6. Other enhancements are contemplated and provided for.

In block 1014, the enhanced target data set is displayed on a second user display. The first and second user displays may correspond to different user display devices (e.g., first user display device 716 and second user display device 718 of FIG. 7). In some embodiments, these display devices correspond to a single physical display device at different points in time. Thus, the reference data set may be displayed on a monitor at a first point in time, and the enhanced data set may be displayed on the monitor afterwards. In some embodiments, the different user display device second user displays correspond to portions of a single display environment on a single display device (using representations such as "windows" of a display "desktop" or regions of a display workspace). In some embodiments, the different display devices correspond to first and second physical displays (e.g., first and second monitors, respectively).

In block 1016, a transaction record of the enhancement is stored. In various embodiments, the record includes a region identifier, an enhancement selection, a data set identifier, a portion of the reference data set, a portion of the enhanced target data set, a modified processing parameter, and/or other suitable elements of the transaction. In some embodiments, storing includes providing the transaction record at a system interface for storage remotely. The transaction record may include a bookmark that records an aspect of the enhancement operation including a description of a data set, a region, an enhancement, or another parameter. The bookmark can be retrieved and used to restore a previous state and to apply previous data sets, region selections, enhancements, and/or parameters to subsequent data sets. The bookmark may serve as a label for indexing as described above with respect to FIGS. 3-6 or may include such a label.

Figure 11:
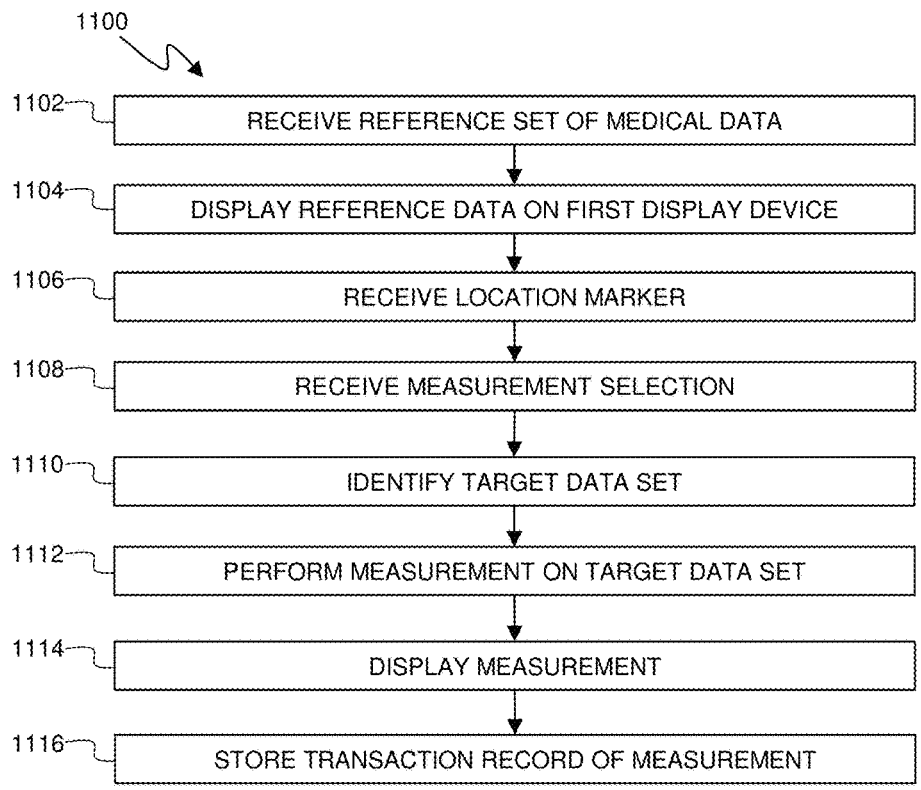
FIG. 11 is a flow diagram of a method of data measurement within a multi-modality processing system according to some embodiments of the present disclosure.

FIG. 11 is a flow diagram of a method 1100 of data measurement within a multi-modality processing system 100 according to some embodiments of the present disclosure. It is understood that additional steps can be provided before, during, and after the steps of method 1100, and some of the steps described can be replaced or eliminated for other embodiments of the method.

In block 1102, a reference set of medical data is received by the multi-modality processing system 100. In some embodiments, an identifier corresponding to the medical data is received either in addition to or as a substitute for receiving the medical data itself. The identifier of the medical data may include some or all of the medical data and/or may include a pointer to data located elsewhere on the system or distributed across a network. The reference set of medical data may be any suitable medical data. In block 1104, the reference set of medical data may be displayed on a first display device. In block 1106, a location marker is received. The location marker may be received from a component of the user interface such as a user input device 714 of FIG. 7 or from a component of the multi-modality system 100 such as a workflow component. As an example of the latter, in an embodiment, a workflow component of the multi-modality system 100 specifies a location marker to alert the operator to relevant diagnostic features such as a vessel wall, a stent, a plaque, a lesion, other characterized tissue, and/or other structures of interest. In some embodiments, a location marker is determined by a combination of user input and system component feedback. For example, a user may specify a first location that is adjusted or snapped to a nearby point of interest identified by a component or module of the multi-modality processing system.

In block 1108, a measurement selection is received. The selection identifies one or more measurements to perform. For example, the selection may specify a distance measurement, an area measurement, a volume measurement, a rate of change measurement, a pinpoint measurement, and/or other suitable measurement.

In block 1110, a target data set is identified. The target data set may depend on the one or more location markers, the measurement selection and/or the reference data set. In some embodiments, the target data set includes a portion of the reference data set. The target data set may also include other data sets either in addition to the reference data set or instead of the reference data set. In such embodiments, the data sets included in the target set may correspond to different modalities, a single modality at different times, a single modality in different operating modes, as well as other combinations of modalities and operating conditions.

In block 1112, a measurement is performed on the target data set by the system 100. In various embodiments, the particular measurement performed is determined by the measurement selection, one or more location marker, and/or the target data set. In an exemplary embodiment, the measurement is a distance measurement and includes performing a conversion from a first coordinate system representative of the user display device (e.g., pixel-based coordinates) to a second coordinate system representative of physical distance (e.g., millimeter-based coordinates). In the particular embodiment, a conversion factor of samples per millimeter and a conversion factor of samples per pixel are received. From this, the number of pixels per millimeters is determined. Then, based on the pixel distance between the location markers, a physical distance can be determined between the corresponding points. In a further exemplary embodiment, the selected measurement operation is a pinpoint measurement, a detailed measurement at a particular point. The analysis may include data interpolation, predictive analysis, the cross-referencing of medical data sets across modalities, and/or other forms of data analysis. The measurement process for determining a pinpoint data value may include data interpolation, predictive analysis, the cross-referencing of medical data sets across modalities, and/or other forms of data analysis. Referring to the measurement of block 1112, other measurement operations including area measurements, volume measurements, rate-of-change measurements, cross-modality measurements, and other measurements known to one of skill in the art are contemplated and provided for.

In block 1114, the value determined by the measurement operation is displayed. As previously described, in some embodiments, the system includes multiple displays. Accordingly, the reference data, the target data, the location markers, and the measured value may be displayed on any one or more of the display devices. In block 1116, a transaction record is created and stored. The transaction record may include information regarding a location marker, a measurement selection, a measured value, a portion of the reference data set, a portion of the target data set, and/or other suitable elements of the transaction. In some embodiments, storing includes providing the transaction record at a system interface for storage remotely. The transaction record may include a bookmark that records an aspect of the measurement operation including a description of a data set, a location marker, a measurement type, a measured value, or another parameter. The bookmark can be retrieved and used to restore a previous state and to apply previous data sets, location markers, measurement types, and/or other parameters to subsequent data sets. The bookmark may serve as a label for indexing as described above with respect to FIGS. 3-6 or may include such a label.

Figure 12:
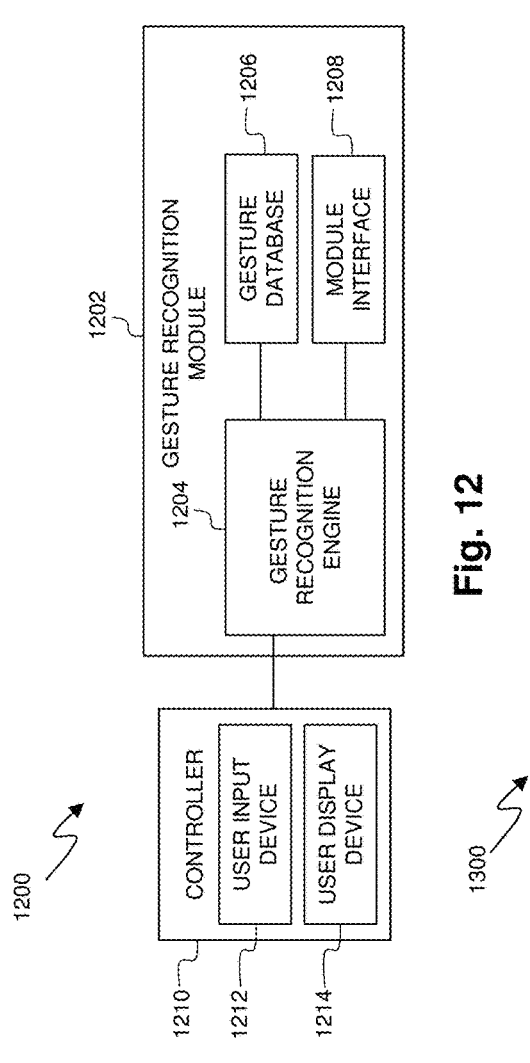
FIG. 12 is a functional block diagram of portions of the medical system of FIGS. 1 and 2, including a user interface component for distinguishing user input according to some embodiments of the multi-modality processing system.

Referring now to FIG. 12, illustrated is a functional block diagram of portions of the medical system of FIGS. 1 and 2, including a user interface component 1200 for distinguishing user input according to some embodiments of the multi-modality processing system 100. The user interface component 1200 converts operator input in the form of gestures into commands for the medical system. Gestures provide an intuitive mechanism for controlling data acquisition, manipulation, and viewing. In some embodiments, gesture recognition allows an operator to select commands without changing input devices, without changing active windows, and/or without navigating a complicated menu structure. Furthermore, in some embodiments, gesture recognition eliminates unnecessary steps and reduces GUI clutter. The streamlined GUI reduces procedure time, which results in better patient outcomes and reduced costs.

The user interface component 1200 includes a gesture recognition module 1202, which may, in turn, contain one or more of a gesture recognition engine 1204, a gesture database 1206, and a module interface 1208 for communicating with other components of the medical system. The user interface component 1200 also includes a controller 1210 or operator interface. The controller 1210 includes a user input device 1212 and one or more user display devices 1214. The user input device 1212 may be substantially similar to the user input device 314 described with respect to FIG. 3. In that regard, examples of suitable user input devices 1212 include, but are in no way limited to, keyboards, keypads, mice, trackballs, digital pens, touch-based interfaces, gesture-based interfaces, verbal and speech-recognition interfaces, adaptive interfaces, cameras, motion-sensing interfaces, and other user input devices known to one of skill in the art.

Portions of the user interface component 1200 may be implemented, in whole or in part, as processor-executable software stored on non-transitory, computer-readable storage media and/or as hardware components such as special purpose microprocessors, FPGAs, microcontrollers, graphics processing units, and DSPs. In some embodiments, portions of the user interface component 1200 are incorporated into components of the multi-modality processing system 100 described with reference to FIGS. 1 and 2. For example, in some such embodiments, controller 1210 is a component of a bedside controller 118, a main controller 120, a boom display 122, and/or a network console 130 described with reference to FIG. 1. As a further example, in some such embodiments, the gesture recognition module 1202 is incorporated into a UI framework service 240 of a main controller 120, a UI framework service 242 of a bedside controller 118, and/or a UI extension such as IVUS UI extension 246 or IVUS UI extension 248 described with reference to FIG. 2. In other embodiments, the gesture recognition module 1202 is a separate and distinct component of the multi-modality processing system 100.

The gesture recognition module 1202 interprets user input(s) based on rules retrieved from the gesture database 1206 and translates the user input(s) into commands. In this way, the module 1202 allows operators to utilize gesture-based inputs to issue commands. Possible gestures include physical gestures and verbal commands. Physical gestures may or may not involve manipulating an input device such as moving an input device or performing a key press. Gestures may also include other interface methods known to one of skill in the art. For reference, the gestures may be captured by any suitable user input device including keyboards, keypads, mice, trackballs, digital pens, touch-based interfaces, verbal and speech-recognition interfaces, adaptive interfaces, cameras, motion-sensing interfaces, and other user input devices known to one of skill in the art.

The gesture recognition module 1202 receives a user input sequence from one or more user input devices 1212. The user input sequence may be divided into discrete elements that represent data collected by the input device 1212, such as a button press, a key press, movement, captured audio, and captured video, and other input data known to one of skill in the art. The user input sequence may also contain formatting data, including device identifiers, device status, device polling, and delimiters. In some embodiments, the user input sequence combines multiple types of data collected from multiple input devices. In such embodiment, a sequence includes data from a keyboard and a mouse. In another such embodiment, a sequence includes data from a pen-based input and a virtual keypad. An exemplary sequence includes a mouse button down event followed by positional data, which is followed by a mouse button up event. A further exemplary input sequence includes a touchstart event, a touchmove event, and a touchend event.

The gesture recognition engine 1204 of the module 1202 assembles a list of active commands to compare to the user input sequences. In some embodiments, the module 1202 receives a system state designator corresponding to a state or mode of operation of the multi-modality processing system. The state designator may indicate a modality. In that regard, an exemplary system state designator indicates that the current data corresponds to one or more of IVUS, FL-IVUS, FFR determination, a coronary flow reserve (CFR) determination, optical coherence tomography (OCT), transesophageal echocardiography, pressure, flow, and/or other suitable modalities. The state designator may also indicate a status of a hardware component, whether medical data is being collected or reviewed, a list of running software components, a status of a software component, a mode of a software component, and/or any other suitable property of the system.

Based on the state designator, the gesture recognition engine 1204 determines the active commands, those commands supported in the current state of the system. In assembling the list of active commands, the engine 1204 may query a gesture database 1206 based on the system state designator. The records of the gesture database 1206 may include one or more of a command name, a command format, a correlated system status, a component to receive the command, and an identifying characteristic of an associated gesture, as well as other suitable information. In some embodiments, the list of active commands depends on the modality or modalities corresponding to the current set of medical data. For example, certain commands may be active during the collection and/or review of data for forward-looking IVUS images (FL-IVUS), while other commands may be active during the collection and/or review of OCT data. Furthermore, in some embodiments, a subset of active commands is common to multiple modalities. For example, some commands related to manipulating images may be uniform across different imaging modalities. Having uniformity across modalities helps simplify the interface, which, in turn, reduces the learning curve and operator burden.

When the list is assembled, the gesture recognition engine 1204 matches one or more elements of the user input sequence to the list of active commands. Elements may be matched based on the identifying characteristics of the active commands. If a match is found, the sequence is translated into a corresponding command or series of commands and presented at the module interface 1208 for use by the appropriate component. In addition to identifying the associated command(s), the translation may include converting one or more elements of the user input sequence into parameters of the command. For example, a set of coordinates obtained from a user input sequence may be passed as a parameter of a command. The coordinates may then be used by a component of the system such as the measurement zoom module 702 described with respect to FIG. 7, the UI framework service 240, the system UI extension 244, a modality extension including IVUS UI extension 246 and modality UI extension 250, and/or other suitable component of the system 100.

As a non-limiting example, one gesture-based command, a poke command, is intended to select a single point and is characterized by a selecting event followed by a movement distance of less than a threshold for unintentional movement. The exemplary poke command passes a set of coordinates derived from the gesture input sequence as a parameter. Another exemplary command, a diameter measurement command, is characterized by a selecting event followed by a movement distance of greater than a threshold for unintentional movement where the movement is within a threshold tolerance of a linear path. The exemplary diameter measurement command passes start and stop coordinates derived from the gesture input sequence as parameters. Another exemplary command, an area measurement command, is characterized by a selecting event followed by a movement distance of greater than a threshold for unintentional movement where the movement exceeds a threshold tolerance of a linear path. The exemplary area measurement command passes a geometric shape approximating a path traced by the gesture input sequence as a parameter.

When the translation is complete, the gesture recognition engine 1204 presents the translated command(s) at the module interface 1208 for use by the appropriate component. In some embodiments, the gesture recognition module 1202 displays the translated command(s) to the operator via the controller 1210 for confirmation prior to presenting the command(s) at the module interface 1208. If the operator confirms the command, it may be presented at the module interface 1208 for use by the system 100. If the operator is not satisfied with the translated command, the gesture recognition module 1202 may cancel and/or modify the command at the operator's request. In some embodiments, the operator can modify elements of the command by further gestures and input. In some such embodiments, the gesture recognition module 1202 presents the operator with reference points that the operator can drag or otherwise manipulate to adjust a location or path. In another such embodiment, the gesture recognition module 1202 presents the operator with a suggested modification to the current command. The suggestion may be based on system defaults, user preference, and/or other criteria. In another such embodiment, the gesture recognition module 1202 presents the operator with a list of alternative commands for the operator to select from. U.S. Provisional Patent Application No. 61/560,677, entitled "MEDICAL SENSING CONTROL SYSTEM AND METHOD", also discloses gestures and gesture translation and is hereby incorporated by reference in its entirety.

Figure 13:
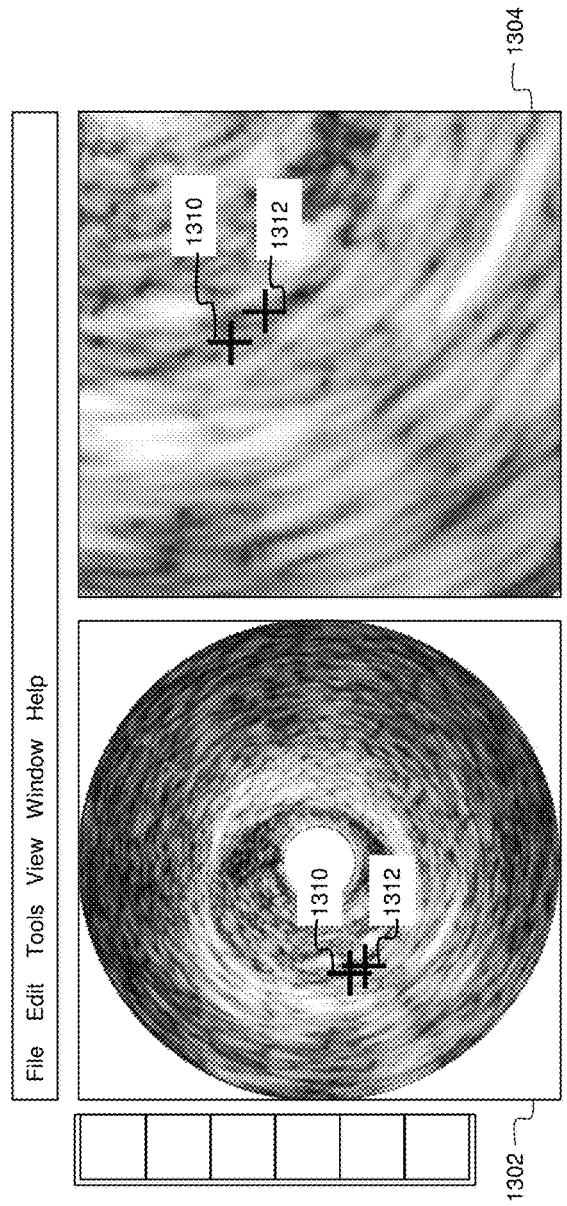
FIG. 13 is a diagram of an exemplary user interface displaying a gesture-based user input sequence according to some embodiments of the multi-modality processing system.
Figure 14:
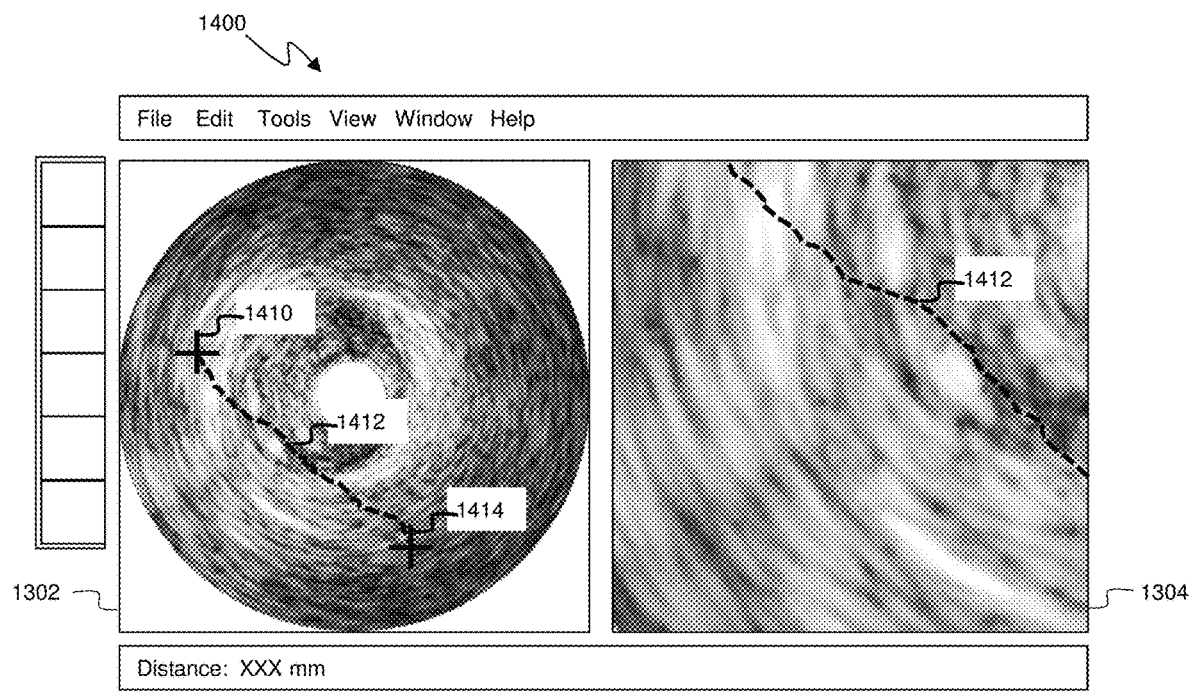
FIG. 14 is a diagram of an exemplary user interface displaying a gesture-based user input sequence according to some embodiments of the multi-modality processing system.
Figure 15:
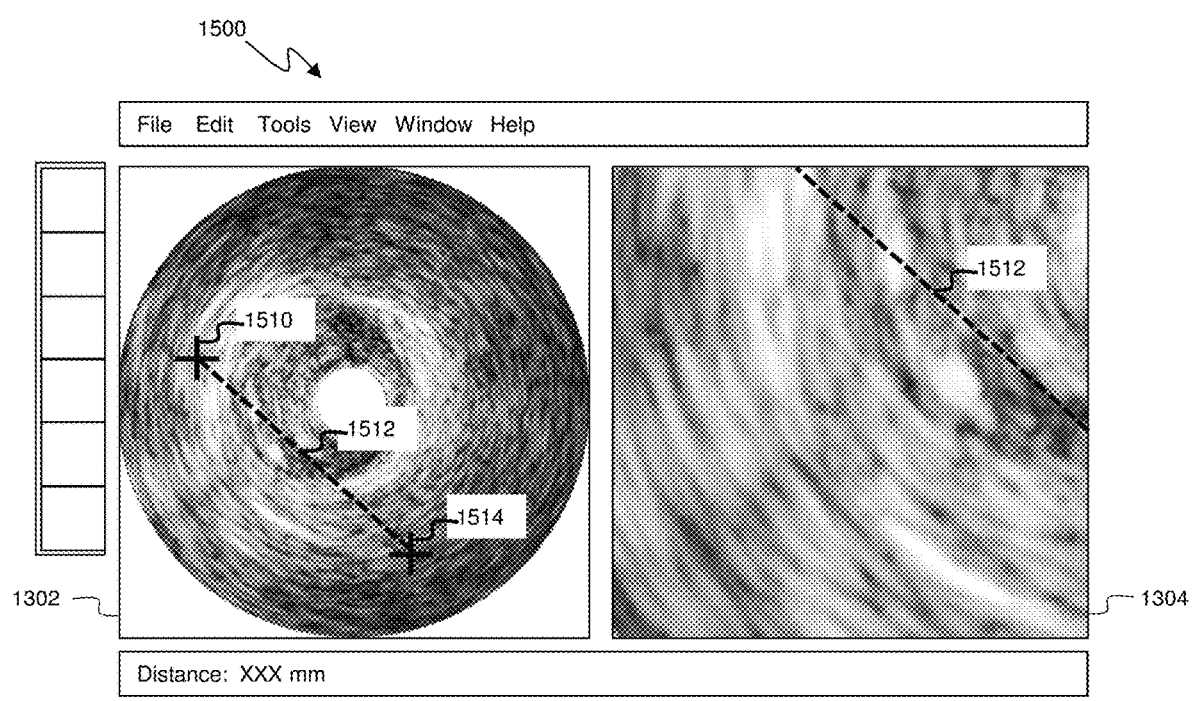
FIG. 15 is a diagram of an exemplary user interface displaying a translated instruction according to some embodiments of the multi-modality processing system.
Figure 16:
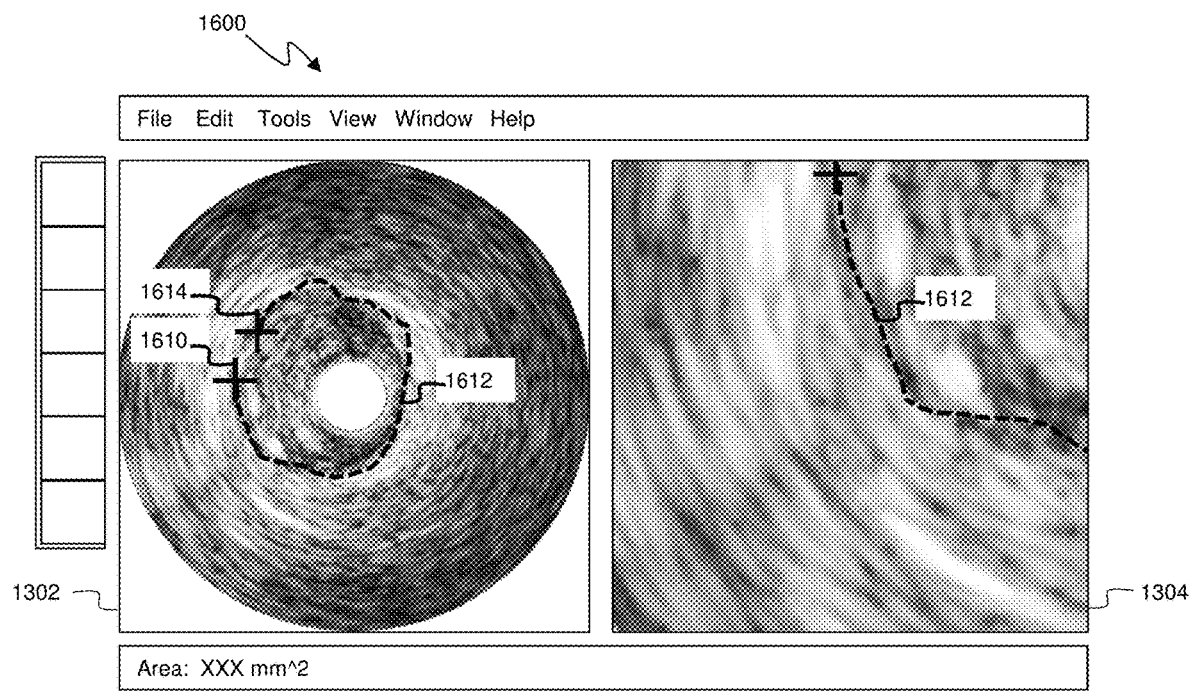
FIG. 16 is a diagram of an exemplary user interface displaying a gesture-based user input sequence according to some embodiments of the multi-modality processing system.
Figure 17:
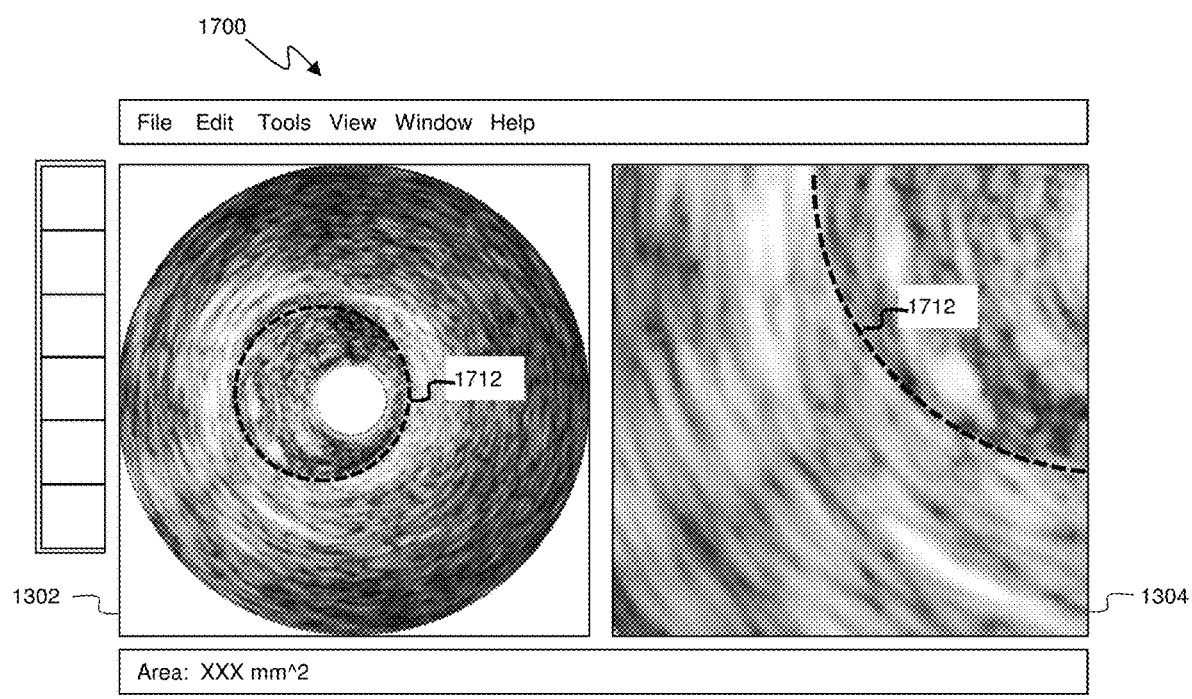
FIG. 17 is a diagram of an exemplary user interface displaying a translated instruction according to some embodiments of the multi-modality processing system.

An exemplary embodiment is described with reference to FIGS. 13-17. FIG. 13 is a diagram of an exemplary user interface 1300 displaying a gesture-based user input sequence according to some embodiments of the multi-modality processing system 100. FIG. 14 is a diagram of an exemplary user interface 1400 displaying a gesture-based user input sequence according to some embodiments of the multi-modality processing system 100. FIG. 15 is a diagram of an exemplary user interface 1500 displaying a translated instruction according to some embodiments of the multi-modality processing system 100. FIG. 16 is a diagram of an exemplary user interface 1600 displaying a gesture-based user input sequence according to some embodiments of the multi-modality processing system 100. FIG. 17 is a diagram of an exemplary user interface 1700 displaying a translated instruction according to some embodiments of the multi-modality processing system 100.

Referring more specifically to FIG. 13, in the illustrated embodiment, a set of medical data is displayed on first user display 1302 and second user display 1304. The gesture recognition module 1202 receives a state designator identifying a modality corresponding to the set of medical data and a mode of operation. The gesture recognition engine 1204 of the module 1202 then queries the gesture database 1206 based on the state designator and receives the active commands. The active commands are added to a list along with identifying characteristics used to recognize the associated gestures.

In some instances, the gesture recognition engine 1204 receives a user input sequence including a touchstart event. In the illustrated embodiment, a marker 1310 is displayed based on the touchstart event. The user input sequence also includes positional data and a touchend event (illustrated by marker 1312). The markers 1310 and 1312 may be displayed on any suitable user display device or devices including the first user display 1302 and the second user display 1304 of FIG. 13. The gesture recognition engine 1204 matches the user input sequence to a gesture based on the identifying characteristics of the active commands. In the example of FIG. 13, a poke command is intended to select a single point and ignores movement of the input device if it is minor and appears unintentional. A threshold may be established for unintentional movement. Accordingly, the identifying characteristics of a poke command include a touchstart event followed by a movement distance of less than the threshold length followed by a touchend event. In the illustrated embodiment, the user input sequence is interpreted as a poke command.

As part of the translation, the gesture recognition engine 1204 determines a set of coordinates to pass as a parameter of the poke command. In various examples, the coordinates are based on the coordinates of the touchstart event, on the coordinates of the touchend event, or a midpoint between the coordinates of the touchstart and the touchend events. In some embodiments, the coordinates may be adjusted by or snapped to a location determined by the system 100. For example, in embodiments where the system 100 supports border detection, a user-specified location may be snapped to a nearby border and the coordinates determined accordingly. Border detection in a medical imaging context is disclosed in U.S. Pat. No. 6,200,268 entitled "VASCULAR PLAQUE CHARACTERIZATION" issued Mar. 13, 2001, U.S. Pat. No. 6,381,350 entitled "INTRAVASCULAR ULTRASONIC ANALYSIS USING ACTIVE CONTOUR METHOD AND SYSTEM" issued Apr. 30, 2002, U.S. Pat. No. 7,074,188 entitled "SYSTEM AND METHOD OF CHARACTERIZING VASCULAR TISSUE" issued Jul. 11, 2006, U.S. Pat. No. 7,175,597 entitled "NON-INVASIVE TISSUE CHARACTERIZATION SYSTEM AND METHOD" issued Feb. 13, 2007, U.S. Pat. No. 7,215,802 entitled "SYSTEM AND METHOD FOR VASCULAR BORDER DETECTION" issued May 8, 2007, U.S. Pat. No. 7,359,554 entitled "SYSTEM AND METHOD FOR IDENTIFYING A VASCULAR BORDER" issued Apr. 15, 2008, and U.S. Pat. No. 7,463,759 entitled "SYSTEM AND METHOD FOR VASCULAR BORDER DETECTION" issued Dec. 9, 2008, the teachings of which are hereby incorporated by reference herein in their entirety.

The translated "poke" command is provided at the module interface 1208 for use by a component of the system such as the measurement zoom module 702 described with respect to FIG. 7, the UI framework service 240, the system UI extension 244, a modality extension including IVUS UI extension 246 and modality UI extension 250, and/or other suitable component of the system 100.

Referring now to FIG. 14, in the illustrated embodiment, the gesture recognition engine receives a different user input sequence after displaying the set of medical data on the first user display 1302 and the second user display device 1304. The exemplary user input sequence includes a touchstart event (illustrated by marker 1410), positional data (illustrated by trace 1412), and a touchend event (illustrated by marker 1414). The markers 1410 and 1414 and the trace 1412 may be displayed on any suitable user display device or devices 1214 including the first user display 1302 and the second user display 1304 of FIG. 14. The gesture recognition engine 1204 matches the user input sequence to a gesture based on the identifying characteristics of the active commands. In the example of FIG. 14, a diameter measurement command is intended to measure a distance in a straight line between two specified points. Accordingly, the identifying characteristics of the command include a movement distance greater than a threshold for unintentional movement and a movement path within a threshold tolerance of a linear path. In the illustrated embodiment, the user input sequence is interpreted as a diameter measurement command.

The gesture recognition engine 1204 may perform further translation such as determining coordinate endpoints based on the user input. In various examples, the coordinate endpoints are based on the coordinates of the touchstart event and/or on the coordinates of the touchend event. In some embodiments, the coordinate endpoints may be adjusted by or snapped to a region determined by the system 100. For example, in embodiments where the system 100 supports border detection, a user-specified location may be snapped to a nearby border and the coordinates determined accordingly. The gesture recognition engine 1204 may also correct or account for abnormalities that would affect the diameter measurement.

Referring now to FIG. 15, in the illustrated embodiment, the translated diameter measurement command described with reference to FIG. 14 is displayed on one or more of the user display device or devices 1214 including first display device 1302 and second display device 1304. This presents the operator an opportunity to verify the translation. In the illustrated embodiment, the first user display 1302 and the second user display 1304 utilize marker 1510 to represent a start point of the command, marker 1514 to represent an endpoint of the command, and trace 1512 to represent the linear path of the command. The operator can confirm the translated command via a user input device 1212. If the command is confirmed by the operator, the command is provided at the module interface 1208 for use by the respective component of the system such as a measurement zoom module 702 described with respect to FIG. 7, the UI framework service 240, the system UI extension 244, a modality extension including IVUS UI extension 246 and modality UI extension 250, and/or other suitable component of the system 100. If the operator is not satisfied with the translated command, the gesture recognition module 1202 may cancel and/or modify the command at the operator's request. For example, the gesture recognition module 1202 may allow the operator to drag the endpoints, may present the operator with other reference points that the operator can manipulate, may present the operator with a suggested modification to the current command, and/or may present a list of alternative commands for the operator to select from.

Referring now to FIG. 16, in the illustrated embodiment, the gesture recognition engine receives another user input sequence based on the set of medical data displayed on the first and second user displays 1302 and 1304. The exemplary user input sequence includes a touchstart event (illustrated by marker 1610), positional data (illustrated by trace 1612), and a touchend event (illustrated by marker 1614). The marker 1610 and 1614 and the trace 1612 may be displayed on any suitable user display device or devices 1214 including the first user display 1302 and the second user display 1304 of FIG. 16. The gesture recognition engine 1204 matches the user input sequence to a gesture based on the identifying characteristics of the active commands. In the example of FIG. 16, an area measurement command is intended to determine an area within a specified boundary. Accordingly, the identifying characteristics of the command include a movement distance greater than a threshold for unintentional movement and a movement path beyond a threshold tolerance of a linear path. In the illustrated embodiment, the user input sequence is interpreted as an area measurement command.

As part of the translation, the gesture recognition engine may perform further interpretation such as determining coordinate endpoints for the command. In various examples, the coordinate endpoints are based on the coordinates of the touchstart event and/or on the coordinates of the touchend event. The gesture recognition engine 1204 may also determine a smoothed geometric path, such as a circular, ovoid, spline, or polygonal path, for the corresponding command. The location, shape, and nature of the geometric path may be determined in part on locations and structures detected and recognized by the system 100. In an exemplary embodiment, a geometric path represented by a circle is resized and shifted to intersect border points as determined by the system 100. In a further exemplary embodiment, an ovoid geometric path is substituted for a circular geometric path in order to more closely intersect one or more border points as determined by the system. In another exemplary embodiment, breakpoints of a spline are adjusted to snap to border points as determined by the system.

Referring now to FIG. 17, in the illustrated embodiment, the translated area measurement command described with reference to FIG. 16 is displayed on one or more of the user display device or devices 1214, providing an opportunity to verify the translation. In the illustrated embodiment, the first user display 1302 and the second user display 1304 utilize trace 1712 to represent the smoothed geometric path of the command. The operator can confirm the translated command via a user input device 1212. If the command is confirmed by the operator, the command is provided at the module interface 1208 for use by the respective component of the system such as a measurement zoom module 702 described with respect to FIG. 7, the UI framework service 240, the system UI extension 244, a modality extension including IVUS UI extension 246 and modality UI extension 250, and/or other suitable component of the system 100. If the operator is not satisfied with the translated command, the gesture recognition module 1202 may cancel and/or modify the command at the operator's request. For example, the gesture recognition module 1202 may present the operator with reference points that the operator can drag or otherwise manipulate to adjust an endpoint or intermediate point, may present the operator with a suggested modification to the current command, and/or may present a list of alternative commands for the operator to select from.

Figure 18:
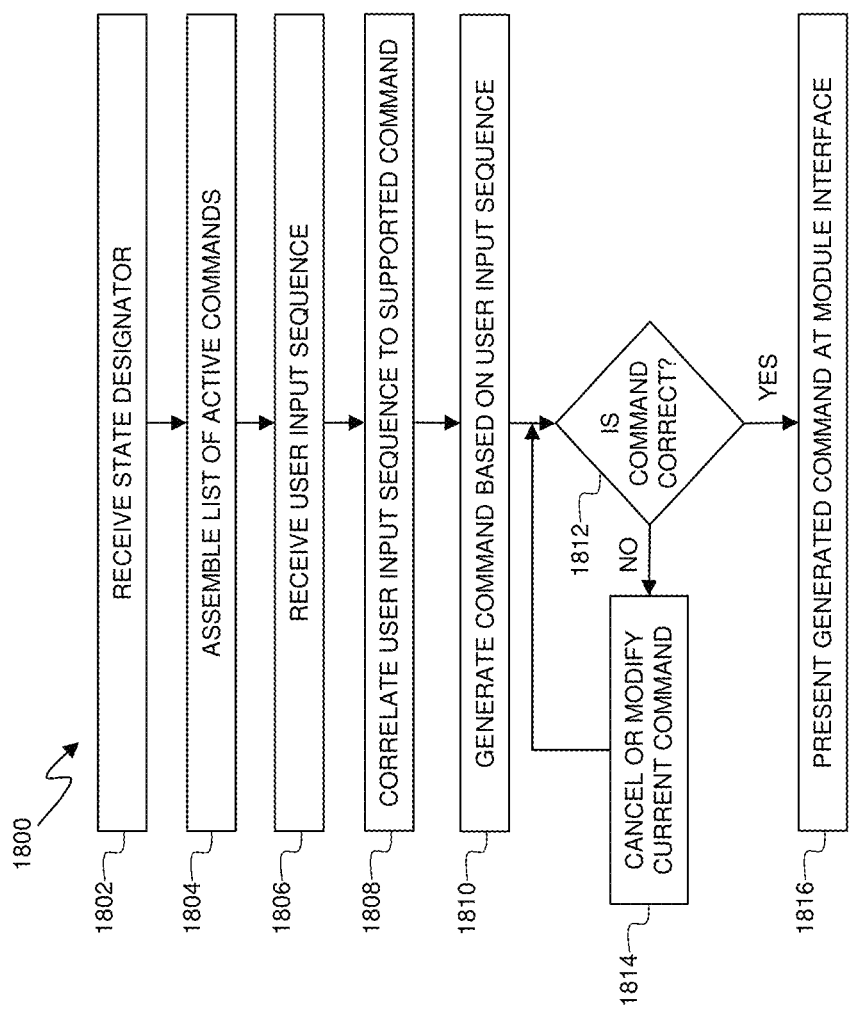
FIG. 18 is a flow diagram of a method of gesture recognition within a multi-modality processing system according to some embodiments of the present disclosure.

FIG. 18 is a flow diagram of a method 1800 of gesture recognition within a multi-modality processing system 100 according to some embodiments of the present disclosure. It is understood that additional steps can be provided before, during, and after the steps of method 1800, and some of the steps described can be replaced or eliminated for other embodiments of the method.

In block 1802, a state designator is received by a component of the system 100 such as the gesture recognition module 1202 of FIG. 12. The state designator may indicate a modality. In that regard, an exemplary system state designator indicates that the current data corresponds to one or more of IVUS, FL-IVUS, FFR determination, a coronary flow reserve (CFR) determination, optical coherence tomography (OCT), transesophageal echocardiography, pressure, flow, and/or other suitable modalities. The state designator may also indicate a status of a hardware component, whether medical data is being collected or reviewed, a list of running software components, a status of a software component, a mode of a software component, and/or any other suitable property of the system.

In block 1804, a list of active commands is assembled. In some embodiments, the list of active commands is based on the state designator. For example, the list may be based on a modality and may include a subset of active commands that apply to multiple modalities. In some embodiments, assembling the list includes querying an electronic database, gesture database 1206, using the state designator. The records of the gesture database 1206 may include one or more of a command name, a command format, a correlated system status, a component to receive the command, and an identifying characteristic of an associated gesture, as well as other suitable information.

In block 1806, a user input sequence is received. The sequence may be received from an suitable user input device, including keyboards, keypads, mice, trackballs, digital pens, touch-based interfaces, verbal and speech-recognition interfaces, adaptive interfaces, cameras, motion-sensing interfaces, and other user input devices known to one of skill in the art. In some embodiments, the user input sequence combines sequences from multiple input devices, for example, a keyboard and a mouse. The sequence may take any suitable form known to one of skill in the art. In an exemplary embodiment, elements of the sequence represent a device state, an event, positional data such as movement data, a speech sample, delimiter, and/or other sequence elements.

In block 1808, the user input sequence is correlated to a command from the supported command list. This may include comparing one or more sequence elements of the user input sequence to the distinguishing criteria of the active commands. It may also include mapping one or more sequence elements to parameters of the corresponding command. In block 1810, the command mapped to the user input sequence is generated. This may include generating values for one or more parameters of the command based on the user input sequence.

In block 1812, the command is displayed on a user display device for confirmation by an operator. This may include receiving a confirmation reply via the user input device 1212. If the operator is not satisfied with the translated command, in block 1814, the command may be canceled and/or modified at the operator's request. In some embodiments, this includes presenting options for modifications to the command and/or receiving further user input specifying the modifications to apply. In some such embodiments, reference points are presented that the operator can drag or otherwise manipulate to adjust a location or path. In another such embodiment, suggested modifications to the current command are presented and a selection is received. The suggestions may be based on system defaults, user preference, and/or other criteria. In another such embodiment, a list of alternative commands is presented and a selection is received. When the operator confirms the command, in block 1816, the command is presented at a module interface 1208 for utilization by an appropriate component of the system.

Figure 19:
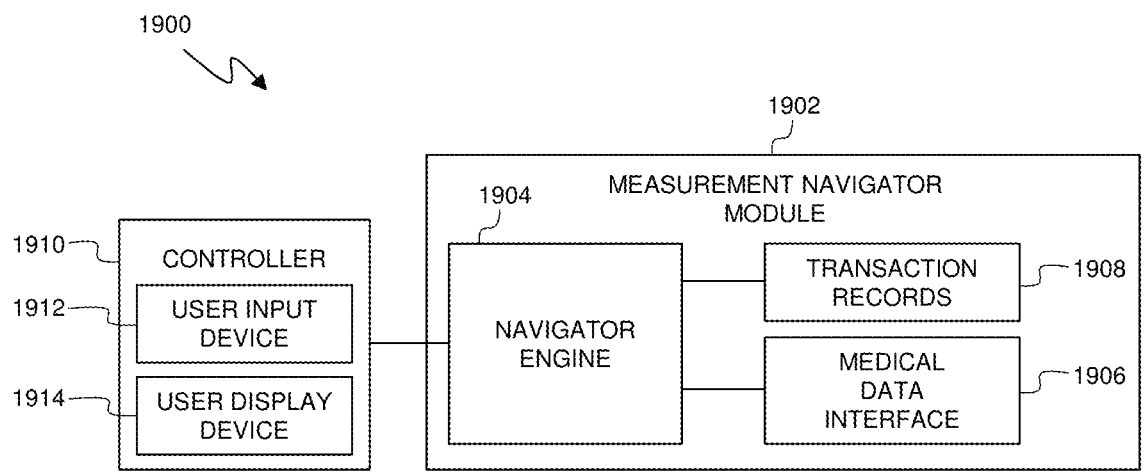
FIG. 19 is a functional block diagram of portions of the medical system of FIGS. 1 and 2, including a user interface component for navigating sets of medical data according to some embodiments of the multi-modality processing system.

FIG. 19 is a functional block diagram of portions of the medical system of FIGS. 1 and 2, including a user interface component 1900 for navigating sets of medical data according to some embodiments of the multi-modality processing system 100. The user interface component 1900 presents a high-level view of a reference set of medical data, from which the operator can select a subset to explore in a detailed view. To create the detailed view, in some embodiments, the user interface component 1900 performs a single-axis zoom, whereby the subset of data is resized along a first axis independent of a second axis. This is particularly useful for medical data sets that include data values plotted over a range of time or distance, or where the data values are periodic. In such data, the peak-to-peak extremes along one axis might not vary substantially as the scaling of the second axis is adjusted.

One example of a data set suitable for single-axis zoom enhancement is fractional flow reserve (FFR) data. FFR is a currently accepted technique for assessing the severity of a stenosis in a blood vessel, including ischemia-causing lesions. FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Further measurements such as Instant Wave-Free Ratio™ Functionality data (iFR® Functionality) (both trademarks of Volcano Corp.) and those disclosed in U.S. patent application Ser. No. 13/460,296, entitled "DEVICES, SYSTEMS, AND METHODS FOR ASSESSING A VESSEL," which discloses the use of pressure ratios that are available without a hyperemic agent, are also suitable for such enhancement. iFR® and FFR data sets may include values corresponding to pressure measurement, pressure ratios, and/or pressure differentials measured over a range of time. By allowing an operator to adjust the scaling of the time axis independent of the pressure or ratio axis, the user interface component 1900 can provide a more useful display of the selected subset to a user.

Additionally, the user interface component 1900 allows the operator to specify a number of data manipulations including data selection, data enhancement, and bookmarking using the high-level and/or the detailed view. In that regard, the user interface component 1900 may incorporate some or all of the functionality of the measurement zoom module 702 described with respect to FIG. 7, the gesture recognition module 1202 described with respect to FIG. 12, and/or other components of the system 100 disclosed herein. Thus, in various embodiments, the user interface component 1900 is capable of performing a variety of data enhancements on the subset of data including zooming, adjusting brightness, adjusting opacity, adjusting a color mask, increasing and decreasing resolution, resampling, interpolating, adjusting gain, and measuring including measuring distance, area, volume, and rate of change. In this way, the user interface component 1900 provides an improved interface for navigating and manipulating data sets in a manner responsive to the nature of the underlying data.

The user interface component 1900 includes a measurement navigator module 1902, which may, in turn, contain one or more of a navigator engine 1904, a medical data interface 1906 for receiving a set of medical data, and an electronic database of transactions, bookmarks, and annotations 1908. The user interface component 1900 also includes a controller 1910 or operator interface. The controller 1910 may include one or more user display devices 1914 and a user input device 1912. The user input device 1912 may be substantially similar to the user input device 314 described with respect to FIG. 3. In that regard, examples of suitable user input devices 1912 include, but are in no way limited to, keyboards, keypads, mice, trackballs, digital pens, touch-based interfaces, gesture-based interfaces, verbal and speech-recognition interfaces, adaptive interfaces, cameras, motion-sensing interfaces, and other user input devices known to one of skill in the art.

Portions of the user interface component 1900 may be implemented, in whole or in part, as processor-executable software stored on non-transitory, computer-readable storage media and/or as hardware components such as special purpose microprocessors, FPGAs, microcontrollers, graphics processing units, and DSPs. In some embodiments, portions of the user interface component 1900 are incorporated into components of the multi-modality processing system 100 described with reference to FIGS. 1 and 2. For example, in some such embodiments, controller 1910 is a component of a bedside controller 118, a main controller 120, a boom display 122, and/or a network console 130 described with reference to FIG. 1. As a further example, in some such embodiments, the measurement navigator module 1902 is incorporated into a UI framework service 240 of a main controller 120, a UI framework service 242 of a bedside controller 118, and/or a UI extension such as IVUS UI extension 246 or IVUS UI extension 248 described with reference to FIG. 2. In other embodiments, the measurement navigator module 1902 is a separate and distinct component of the multi-modality processing system 100.

The measurement navigator module 1902 receives a reference set of medical data via the medical data interface 1906. In some embodiments, an identifier corresponding to the medical data is received either in addition to or as a substitute for receiving the medical data itself. The identifier of the medical data may include some or all of the medical data and/or may include a pointer to data located elsewhere on the system or distributed across a network. The reference data set may also be displayed on a display device of the controller 1910 (e.g., the user display device 1914) for the operator to view. The control of the display and the data handling may be performed by the measurement navigator module 1902 directly and/or by other components of the multi-modality processing system 100 separate from the measurement navigator module 1902. In some embodiments, the reference data is presented as a graph, such as a timeline or a plot over distance, although other formats for displaying the data are contemplated including two dimensional and three-dimensional images.

The reference set of medical data may be any suitable medical data. In some embodiments, the medical data includes unprocessed medical data and may be provided by a modality acquisition component (e.g., a fractional flow reserve acquisition component, an iFR acquisition component, a pressure acquisition component, a flow acquisition component, an IVUS acquisition component 220 of FIG. 2, a forward-looking IVUS acquisition component, an FFR acquisition component, a CFR acquisition component, an OCT acquisition component, and/or a transesophageal echocardiography acquisition component). In some embodiments, the medical data includes processed medical data and may be provided by a workflow component (e.g., a fractional flow reserve workflow component, an iFR workflow component, a pressure workflow component, a flow workflow component, an IVUS workflow component, a forward-looking IVUS workflow component, an FFR workflow component, a CFR workflow component, an OCT workflow component, and/or a transesophageal echocardiography workflow component). In some embodiments, the medical data includes data aggregated from multiple modalities and may be provided by a multi-modality workflow component.

The measurement navigator module 1902 also receives one or more navigation commands, such as a data selection indicating a portion of the reference set of medical data, an enhancement selection, a bookmark command, zoom-in and zoom-out commands, and other suitable navigation commands. Based on the navigation commands and/or the reference set of medical data, the navigator engine 1904 determines a subset of the reference medical data to enhance. The subset may include all or a portion of the reference set. The subset may also include alternate data sets either in addition to the reference data set or instead of the reference data set. In such embodiments, the data sets included in the subset may correspond to different modalities, a single modality at different times, a single modality in different operating modes, as well as other combinations of modalities and operating conditions. With respect to some types of data selection commands, the navigation command may be converted from an initial format to a data format. For example, a navigation command may include a set of rectangular coordinates corresponding to pixels of a user display device 1914. Accordingly, in an embodiment, the navigator engine 1904 of the module 1902 converts pixel coordinates into data values. This may include one or more conversions such as scale conversion, coordinate conversion, shape translation, and other suitable conversions known to one of skill in the art.

In some embodiments, the navigation commands are operator commands and are received via the user input device 1912. In one such embodiment, a gesture interface (e.g., gesture recognition module 1202 of FIG. 12) in communication with the user input device 1912 and the measurement navigator module 1902 receives a gesture from the user input device 1912, translates the gesture into a navigation command, and provides the navigation command to the measurement navigator module 1902. In a further such embodiment, the measurement navigator module 1902 incorporates some or all of the gesture recognition module 1202. Navigation commands may also be received from another system component such as a modality workflow component. For example, in an exemplary embodiment, the measurement navigator module 1902 receives a data selection indicating a portion of the medical data from an FFR workflow component. The data selection may be configured to highlight, display, and/or otherwise draw attention to a value of interest detected by the workflow component such as a peak FFR value, a value exceeding a threshold, and/or a value indicating a sensor malposition. In another exemplary embodiment, the measurement navigator 1902 receives a bookmark from the FFR workflow component. The bookmark may be configured to provide a point of reference for quickly locating a value of interest detected by the workflow component. Such behavior allows components of the system to alert the operator to potentially important data that might otherwise go unnoticed.

As previously discussed, the measurement navigator module 1902 may receive navigator commands that specify one or more enhancement functions to perform. Examples of suitable enhancements include zooming, adjusting brightness, adjusting opacity, adjusting a color mask, increasing and decreasing resolution, resampling, interpolating, adjusting gain, and measuring including measuring distance, area, volume, and rate of change. Enhancements may also include labeling or annotating a portion of the medical data, such as the labeling described with respect to FIGS. 3-6. Other suitable enhancements include a single-axis zoom. Unlike a two-axis zoom, the navigator engine 1904 may resize, resample, or otherwise enhance data along a first axis, such as a time axis, independent of a second axis, such as a pressure or velocity axis. In one such embodiment, a reference data set corresponding to FFR measurements includes pressure data points over a range of time. An operator selects to perform a single-axis zoom and specifies start and stop time boundaries and accordingly a new range. In response, the navigator engine 1904 scales the subset of data indicated by the new range along the time axis, but not necessarily along the pressure axis. Instead, in the exemplary embodiment, the pressure axis is rescaled based on maximum and minimum pressure values over the new range. In a related embodiment, the navigator engine 1904 scales the subset of data along the time axis, but does not rescale the pressure axis from that of the reference set. In a further set of embodiments, the measurement navigator engine 1904 performs a single-axis zoom of iFR® imaging data. The operator selects a single-axis zoom and start and stop time boundaries. The navigator engine 1904 rescales the subset described by the start and stop time boundaries along a time axis, but in various embodiments, rescales the pressure axis independently or does not rescale the pressure axis relative to the reference set. By supporting single-axis manipulations in addition to or instead of two-axis manipulations, the navigator engine 1904 provides a more useful representation of certain types of data corresponding to certain modalities. In that regard, in various embodiments, a single-axis manipulation is performed on FFR data, iFR data, pressure data, flow data, and/or other suitable datasets in order to present a more useful representation of the enhanced data.

As with data-specifying commands, commands that specify the type of enhancement to be made may also be received from the user input device 1912 and/or from another component of the system. As the specified enhancement may be performed by the measurement navigator module 1902 and/or another component of the system, such as the measurement zoom module 702, the UI framework service 240, the system UI extension 244, a modality extension including IVUS UI extension 246 and modality UI extension 250, and/or other suitable component of the system 100, the measurement navigator module 1902 may forward the enhancement selection command to the appropriate system component. For example, in performing some enhancements, the navigator engine 1904 may directly or indirectly combine data sets to form the subset. Accordingly, in one embodiment, the navigator engine 1904 provides a command that instructs an MMCM component to combine data sets collected by two or more modalities. In a related embodiment, the navigator engine 1904 receives data sets collected by the two or more modalities and performs the combination within the engine 1904. Similarly, in performing some enhancements, the navigator engine 1904 may cull data sets in order to improve responsiveness and/or reduce the burden on storage, networking, and/or processing resources. In one such embodiment, the navigator engine 1904 culls data outside the selected subset.

Once the type of enhancement to be performed has been determined, the measurement navigator module 1902 may then perform the enhancement on the subset of medical data as instructed by the navigation command. Thereafter, the enhanced subset may be displayed on a user display device. In some embodiments, the reference data and the enhanced subset of data may be displayed on different user display devices (e.g., first user display device and second user display device, respectively). In some embodiments, these display devices correspond to a single physical display device at different points in time. Thus, the reference data set may be displayed on a monitor at a first point in time, and the enhanced data may be displayed on the monitor at a later time. In some embodiments, these display devices correspond to portions of a single display environment on a single display device (using representations such as "windows" of a display "desktop" or regions of a display workspace). In some embodiments, the first and second display devices correspond to first and second physical displays (e.g., first and second monitors, respectively). Displaying the reference data and the enhanced subset of data on different user display devices may be especially helpful in applications where user input may obscure part of a display such as touchscreen applications. In some embodiments, the measurement navigator module 1902 updates the display of the reference data set based on the navigation commands. This may include adding icons to indicate labels, bookmarks, boundaries of the selected subset, and other points of interest. The display may also be update to include shading to indicate data within or outside the selected subset. As previously mentioned, the generation of the display signal corresponding to the reference data and the enhanced subset may be performed by the measurement navigator module 1902 directly, and/or by other components of the multi-modality processing system 100 separate from the measurement navigator module 1902.

The measurement navigator module 1902 may also provide an interface for storing a transaction record. A transaction record may include a region identifier, an enhancement selection, a data set identifier, a portion of the reference data set, a portion of the enhanced subset, a modified processing parameter, and/or other suitable elements of the transaction. The transaction record may be stored within the transaction records database 1908 or provided for transmission and/or storage by components of the system such as the database management component 216 described with respect to FIG. 2. In some embodiments, the transaction record includes a bookmark that records an aspect of the enhancement operation including a description of a data set, a region, an enhancement, or another parameter. The bookmark can be retrieved and used to restore a previous state and to apply previous data sets, region selections, enhancements, and/or parameters to subsequent data sets. The bookmark may serve as a label for indexing as described above with respect to FIGS. 3-6 or may include such a label.

Figure 20:
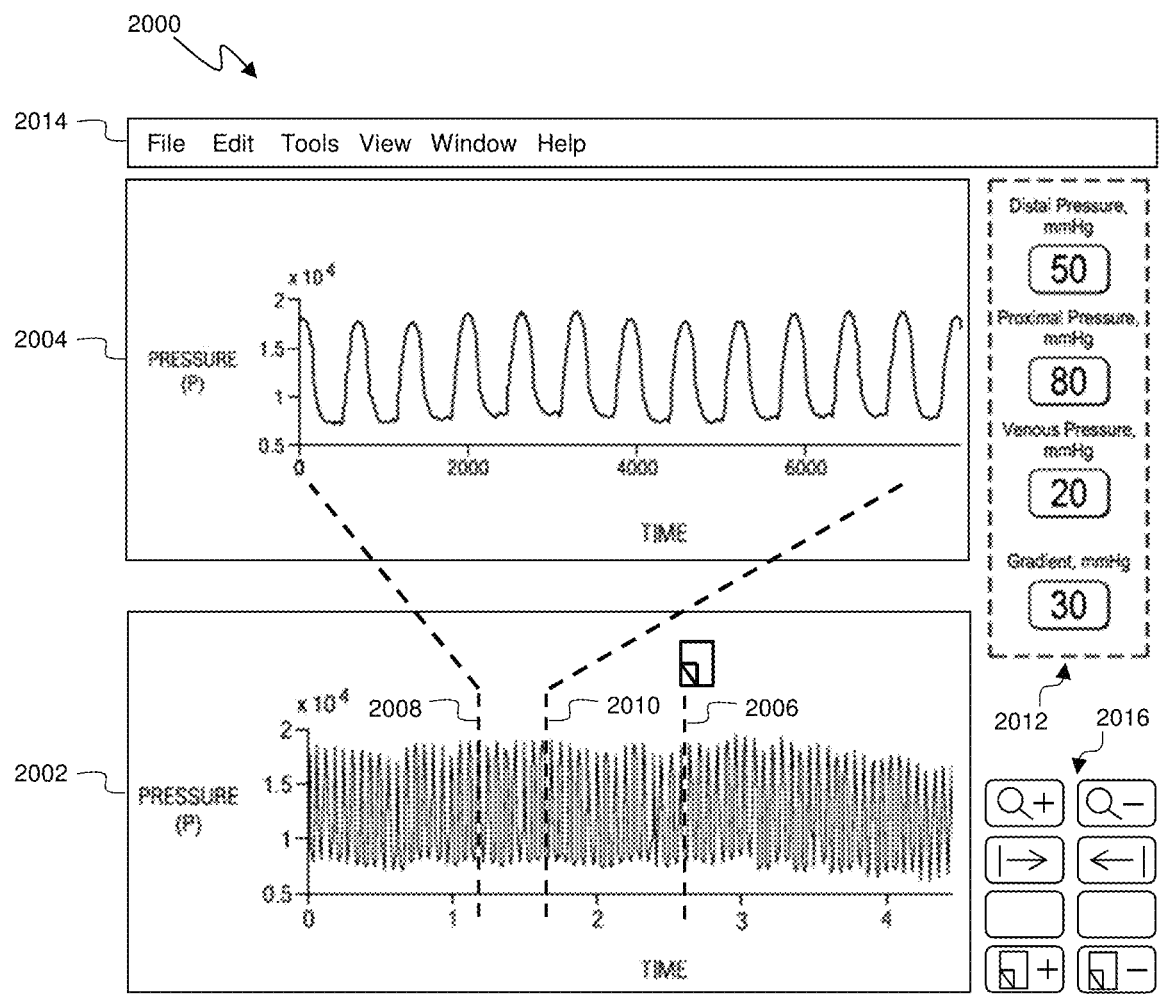
FIG. 20 is a diagram of an exemplary user interface for data navigation and enhancement according to some embodiments of the multi-modality processing system.

FIG. 20 is a diagram of an exemplary user interface 2000 for data navigation and enhancement according to some embodiments of the multi-modality processing system 100. The user interface 2000 may be presented on a single user display or multiple displays. The user interface 2000 represents one possible arrangement for displaying the information presented by the multi-modality processing system and more specifically the measurement navigator module 1902 of the system. One skilled in the art will recognize that alternate arrangements are both contemplated and provided for.

The interface 2000 may include a first data display window 2002 and a second data display window 2004, which may correspond to different display devices, a single physical display device at different points in time, different portions of a single display environment on a single display device (using representations such as "windows" of a display "desktop" or regions of a display workspace), and/or different physical displays (i.e., different monitors). In the illustrated embodiment, the first data display window 2002 presents a reference data set in a first window of a desktop and the second data display window 2004 presents an enhanced subset of the reference data set in a second window of the desktop. In the illustrated embodiment, the enhanced subset has undergone a single-axis zoom procedure. In other words, the enhanced subset has been rescaled along a first axis (the time axis) independent of a second axis (the pressure axis).

In some embodiments, one or more of the first data display window 2002 and the second data display window 2004 include bookmark icons 2006, subset boundary icons 2008 and 2010, and other annotations. The boundary icons 2008 and 2010 may mark the outer bounds the subset along an axis (the time axis in the illustrated embodiment). In some embodiments, the subset is identified by shading regions within or outside the subset.

The interface 2000 may also include one or more auxiliary display regions 2012 for displaying medical data such as values from the reference set of data and/or the enhanced subset. In some embodiments, the interface 2000 includes a toolbar 2014. In various such embodiments, the toolbar 2014 is used to select commands for the multi-modality processing system. Exemplary commands include selection of a subset to enhance, selection of an enhancement to perform, as well as data store and load commands. The interface may also include a number of command elements 2016 for quickly selecting commands to send to the multi-modality processing system. Any command that may be selected from a toolbar is suitable for selection using a command element 2016. In that regard, in an exemplary embodiment, the interface 2000 includes command elements 2016 configured to adjust the boundaries of the subset, set and restore bookmarks, label data values, and zoom-in or zoom-out of the reference set and/or the subset.

Figure 21:
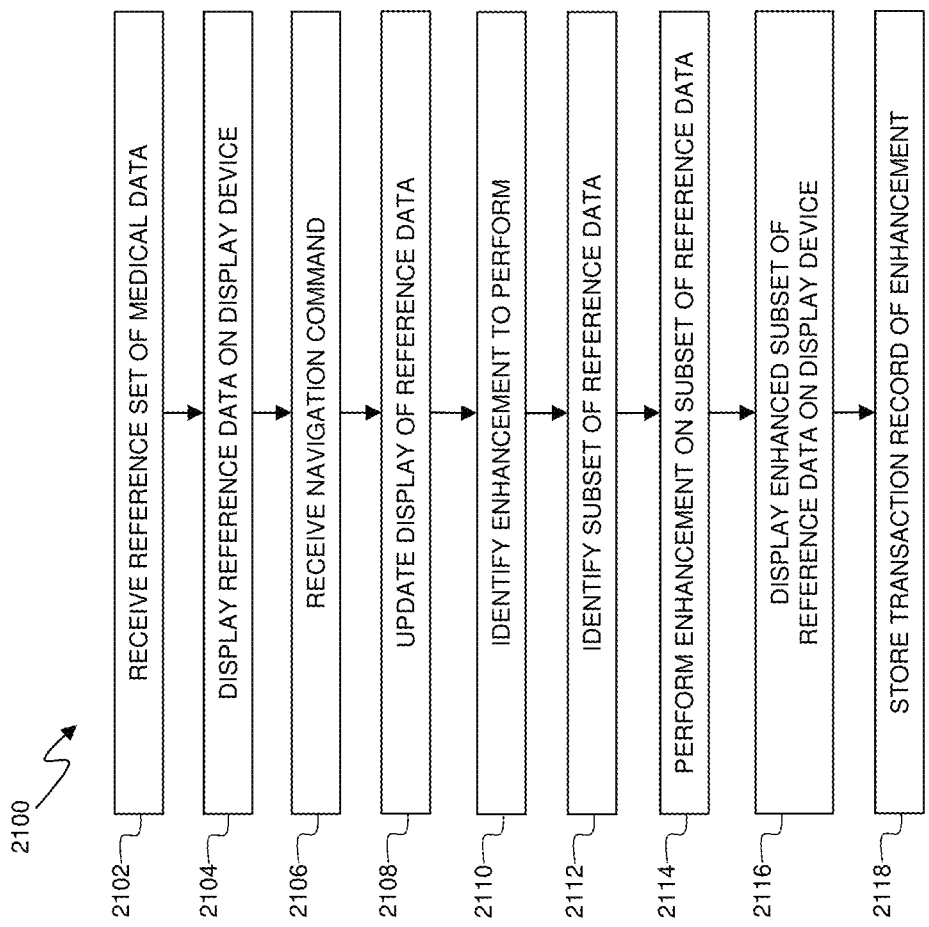
FIG. 21 is a flow diagram of a method of navigating and enhancing sets of medical data within a multi-modality processing system according to some embodiments of the present disclosure.

FIG. 21 is a flow diagram of a method 2100 of navigating and enhancing sets of medical data within a multi-modality processing system according to some embodiments of the present disclosure. It is understood that additional steps can be provided before, during, and after the steps of method 2100, and some of the steps described can be replaced or eliminated for other embodiments of the method.

In block 2102, a reference set of medical data is received by the multi-modality processing system 100. The reference set of medical data may be any suitable medical data. For example, the medical data may include unprocessed medical data provided by a modality acquisition component, processed medical data provided by a workflow component, and/or aggregate data corresponding to multiple modalities and provided by a multi-modality component. In some embodiments, an identifier corresponding to the medical data is received either in addition to or as a substitute for receiving the medical data itself. The identifier of the medical data may include some or all of the medical data and/or may include a pointer to data located elsewhere on the system or distributed across a network. In block 2004, the reference set of medical data may be displayed on a display device.

In block 2106, a navigation command is received. Navigation commands may define a subset to enhance, may select an enhancement to perform, may set or restore a bookmark, may apply a label, and may perform other suitable navigation tasks. In some exemplary embodiments, a gesture recognition module (e.g., the gesture recognition module 1202 of FIG. 12), incorporated into the measurement navigator module 1902 and/or in communication therewith, receives a touch-based input sequence from a user input device 1912. The exemplary touch-based input sequence indicates a first touch at a first location and concurrent a second touch at a second location. The gesture recognition module translates the input sequence into a command to perform a single-axis zoom on a subset corresponding to the region between first touch location and the second touch location. Thus, the navigation command designates a range for the subset having a first boundary corresponding to the first touch location and a second boundary corresponding to the second touch location. The gesture recognition module provides the translated command to a measurement navigator module 1902. While a single-axis zoom is provided as an example, any type of enhancement of the data may be implemented using this method.

In block 2108, the display of the reference set of medical data may be updated based on the received navigation command. For example, the display may be updated to include icons that indicate labels, bookmarks, boundaries of the selected subset, and other points of interest. In some embodiments, the display is updated to include shading to indicate data within or outside the selected subset.

In block 2110, the enhancement to be performed may be identified. The enhancement may be based on one or more navigation commands and/or the reference set of data. In block 2112, a subset of the reference set of data to be enhanced is identified. Similar to the enhancement, the subset may depend on one or more navigation commands and/or the reference set of data. The subset of data may include some or all of the reference set and may also include alternate data sets either in addition to or instead of the reference data set. In such embodiments, the data sets included in the subset may correspond to different modalities, a single modality at different times, a single modality in different operating modes, as well as other combinations of modalities and operating conditions. In some embodiments, the enhancement includes the co-registration of data corresponding to multiple different modalities. Co-registration across different modalities is disclosed in further detail in U.S. Pat. No. 7,930,014 entitled "VASCULAR IMAGE CO-REGISTRATION" issued Apr. 19, 2011, and U.S. Pat. Pub. No. 2007/0038061 entitled "THREE DIMENSIONAL CO-REGISTRATION FOR INTRAVASCULAR DIAGNOSIS AND THERAPY" filed Jun. 23, 2006, the teachings of which are hereby incorporated by reference herein in their entirety. In some embodiments, the method includes directly or indirectly combining data sets to form the subset. Likewise, in some embodiments the method includes culling portions of the subset. In one such embodiment, the method includes culling data outside a selected region.

In block 2114, an enhancement is performed on the subset of data set by the system 100. In various embodiments, the enhancement is determined by one or more navigation commands and/or the reference set of data. Suitable enhancements include, and are not limited to, zooming, adjusting brightness, adjusting opacity, adjusting a color mask, increasing and decreasing resolution, resampling, interpolating, adjusting gain, and measuring including measuring distance, area, volume, and rate of change. Enhancements may also include labeling or annotating a portion of the medical data, such as the labeling described with respect to FIGS. 3-6. Other enhancements are both contemplated and provided for. As a further example, in some embodiments, the enhancement includes a single-axis zoom, whereby the subset of data is resized along a first axis independent of a second axis.

In block 2116, the enhanced data subset is displayed. The reference data and the enhanced subset may be displayed on different user display devices (e.g., a first user display device and a second user display device). In some embodiments, these display devices correspond to a single physical display device at different points in time. Thus, the reference data set may be displayed on a monitor at a first point in time, and the enhanced subset may be displayed on the monitor afterwards. In some embodiments, these display devices correspond to portions of a single display environment on a single display device (using representations such as "windows" of a display "desktop" or regions of a display workspace). In some embodiments, the first and second display devices correspond to first and second physical displays (e.g., first and second monitors, respectively).

In block 2118, a transaction record of the enhancement is stored. In various embodiments, the record includes a region identifier, an enhancement selection, a data set identifier, a portion of the reference data set, a portion of the enhanced subset, a modified processing parameter, and/or other suitable elements of the transaction. In some embodiments, storing includes providing the transaction record at a system interface for storage remotely. The transaction record may include a bookmark that records an aspect of the enhancement operation including a description of a data set, a region, an enhancement, or another parameter. The bookmark can be retrieved and used to restore a previous state and to apply previous data sets, region selections, enhancements, and/or parameters to subsequent data sets. The bookmark may serve as a label for indexing as described above with respect to FIGS. 3-6 or may include such a label.

Although illustrative embodiments have been shown and described, a wide range of modification, change, and substitution is contemplated in the foregoing disclosure and in some instances, some features of the present disclosure may be employed without a corresponding use of the other features. Further, as described above, the components and extensions described above in association with the multi-modality processing system may be implemented in hardware, software, or a combination of both. The processing systems may be designed to work on any specific architecture. For example, the systems may be executed on a single computer, local area networks, client-server networks, wide area networks, internets, hand-held and other portable and wireless devices and networks. It is understood that such variations may be made in the foregoing without departing from the scope of the present disclosure. Accordingly, it is appropriate that the appended claims be construed broadly and in a manner consistent with the scope of the present disclosure.

What is claimed is:

1. An apparatus, comprising:
an intravascular catheter or guidewire comprising at least one of a pressure sensor or a flow sensor; and
a processor configured for communication with the intravascular catheter or guidewire, wherein the processor is configured to:
receive medical data obtained by the intravascular catheter or guidewire while the intravascular catheter or guidewire is positioned within a vessel of a patient, wherein the medical data comprises at least one of pressure data obtained by the pressure sensor or flow data obtained by the flow sensor;
output, to a display in communication with the processor, a first graphical representation of the medical data, wherein the first graphical representation comprises a waveform of the medical data;
receive, from an input device, a selection of a region of the waveform associated with a subset of the medical data;
in response to the selection of the region, automatically perform an enhancement of the subset of the medical data to generate a second graphical representation, wherein the enhancement comprises a resealing of the region of the waveform such that the second graphical representation comprises only the region of the waveform that has been resealed; and
output, to the display, the second graphical representation.

2. The apparatus of claim 1, wherein the second graphical representation represents a single-axis zoomed view of the region of the first graphical representation.

3. The apparatus of claim 1, wherein the processor is configured to receive, from the input device, the selection of the region of the first graphical representation by receiving an input associated with a first boundary of the subset and a second boundary of the subset, and wherein the processor is configured to output, to the display, a first boundary marker indicating the first boundary on the first graphical representation, and a second boundary marker indicating the second boundary of the first graphical representation.

4. The apparatus of claim 1, wherein the processor is configured to:
output, to the display, a screen display comprising:
the first graphical representation; and
the second graphical representation.

5. The apparatus of claim 4, wherein the resealing of the region of the waveform comprises at least one of zoom-in on the subset of the medical data or zoom-out on the subset of the medical data.

6. The apparatus of claim 1, further comprising the input device, wherein the input device comprises a touch screen of the display, wherein the processor is configured to receive the selection by receiving a touch input from the touch screen.

7. The apparatus of claim 4, wherein the screen display further comprises an auxiliary data region including one or more numerical values of the medical data.

8. The apparatus of claim 1, wherein the processor is further configured:
receive, from the input device, a command to adjust a boundary of the subset; and
adjust a boundary of the subset in response to the command.

9. The apparatus of claim 1, wherein the processor is further configured:
receive, from the input device, a command to add a bookmark of the medical data; and
add a bookmark of the medical data in response to the command.

10. The apparatus of claim 1, wherein the processor is further configured:
receive, from the input device, a command to label a data value of the medical data; and
label a data value of the medical data in response to the command.

* * * * *